(12) United States Patent
Govari

(10) Patent No.: US 10,330,742 B2
(45) Date of Patent: Jun. 25, 2019

(54) TRIPLE AXIS SENSOR ON A SINGLE LAYER PRINTED CIRCUIT

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/390,388

(22) Filed: Dec. 23, 2016

(65) Prior Publication Data

US 2018/0180684 A1 Jun. 28, 2018

(51) Int. Cl.
   *G01R 33/02* (2006.01)
   *A61B 1/04* (2006.01)
   (Continued)

(52) U.S. Cl.
   CPC ............ *G01R 33/0206* (2013.01); *A61B 1/04* (2013.01); *G01R 33/0005* (2013.01); *G01R 33/0052* (2013.01); *H01F 5/003* (2013.01); *H01F 41/041* (2013.01); *H05K 1/028* (2013.01); *H05K 1/115* (2013.01); *H05K 1/118* (2013.01); *H05K 1/144* (2013.01); *H05K 1/165* (2013.01); *H05K 3/103* (2013.01); *H05K 3/20* (2013.01); *H05K 3/4038* (2013.01); *H05K 2201/0154* (2013.01); *H05K 2201/051* (2013.01); *H05K 2201/056* (2013.01); *H05K 2201/096* (2013.01);
   (Continued)

(58) Field of Classification Search
   CPC .............................................. H01L 2924/01079
   USPC ........................................................ 174/261
   See application file for complete search history.

(56) References Cited

U.S. PATENT DOCUMENTS 6,097,976 A     8/2000  Yang et al.
6,320,382 B1 *  11/2001 Anderson ............ G01R 33/385
                                                    324/309
(Continued)

FOREIGN PATENT DOCUMENTS

EP        1671669 A1   6/2006
EP        1714610 A1   10/2006
           (Continued)

OTHER PUBLICATIONS

European Search Report dated Apr. 23, 2018, Application No. EP 17 21 0158.

*Primary Examiner* — Hoa C Nguyen
*Assistant Examiner* — Stanley Tso

(57) ABSTRACT

Apparatus, including a flexible insulating substrate, having a first side and a second side, rolled about an axis parallel to the substrate. The apparatus also includes a first conducting spiral that is right-handed relative to a normal to the substrate, and a second conducting spiral that is left-handed relative to the normal, formed on the first side of the substrate. The first conducting spiral has a first initial termination and a first final termination, the second conducting spiral has a second initial termination and a second final termination, the spirals have a displacement therebetween, with a preset magnitude so that when the substrate is rolled about the axis the first initial termination aligns with the second initial termination. The apparatus also has a via penetrating the substrate from the first side to the second side so as to interconnect the first initial termination and the second initial termination.

10 Claims, 18 Drawing Sheets

(51) Int. Cl.
*H05K 1/02* (2006.01)
*G01R 33/00* (2006.01)
*H01F 5/00* (2006.01)
*H01F 41/04* (2006.01)
*H05K 1/11* (2006.01)
*H05K 1/14* (2006.01)
*H05K 1/16* (2006.01)
*H05K 3/10* (2006.01)
*H05K 3/20* (2006.01)
*H05K 3/40* (2006.01)

(52) U.S. Cl.
CPC ............ *H05K 2201/09445* (2013.01); *H05K 2201/09672* (2013.01); *H05K 2201/10151* (2013.01)

(56) References Cited

U.S. PATENT DOCUMENTS

| | | | |
|---|---|---|---|
| 6,998,813 | B2 | 2/2006 | Heizmann et al. |
| 7,229,437 | B2 | 6/2007 | Johnson et al. |
| 7,518,374 | B1 | 4/2009 | Olsson et al. |
| 8,147,486 | B2 | 4/2012 | Honour et al. |
| 8,560,086 | B2 | 10/2013 | Just et al. |
| 9,037,264 | B2 | 5/2015 | Just et al. |
| 9,687,297 | B2 | 6/2017 | Just et al. |
| 2002/0103445 | A1 | 8/2002 | Campbell et al. |
| 2012/0029343 | A1 | 2/2012 | Wasson et al. |
| 2013/0066194 | A1* | 3/2013 | Seter ............ A61B 5/062 600/424 |
| 2015/0303706 | A1 | 10/2015 | Bronson et al. |
| 2015/0327923 | A1 | 11/2015 | Hall et al. |
| 2016/0113712 | A1 | 4/2016 | Cheung et al. |
| 2017/0319270 | A1 | 11/2017 | Hall et al. |
| 2018/0071017 | A1 | 3/2018 | Bar-Tal et al. |
| 2018/0110562 | A1 | 4/2018 | Algawi et al. |

FOREIGN PATENT DOCUMENTS

| | | |
|---|---|---|
| WO | WO 2014/116853 A1 | 7/2014 |
| WO | WO 2016/061673 A1 | 4/2016 |
| WO | WO 2016/083839 A1 | 6/2016 |

* cited by examiner

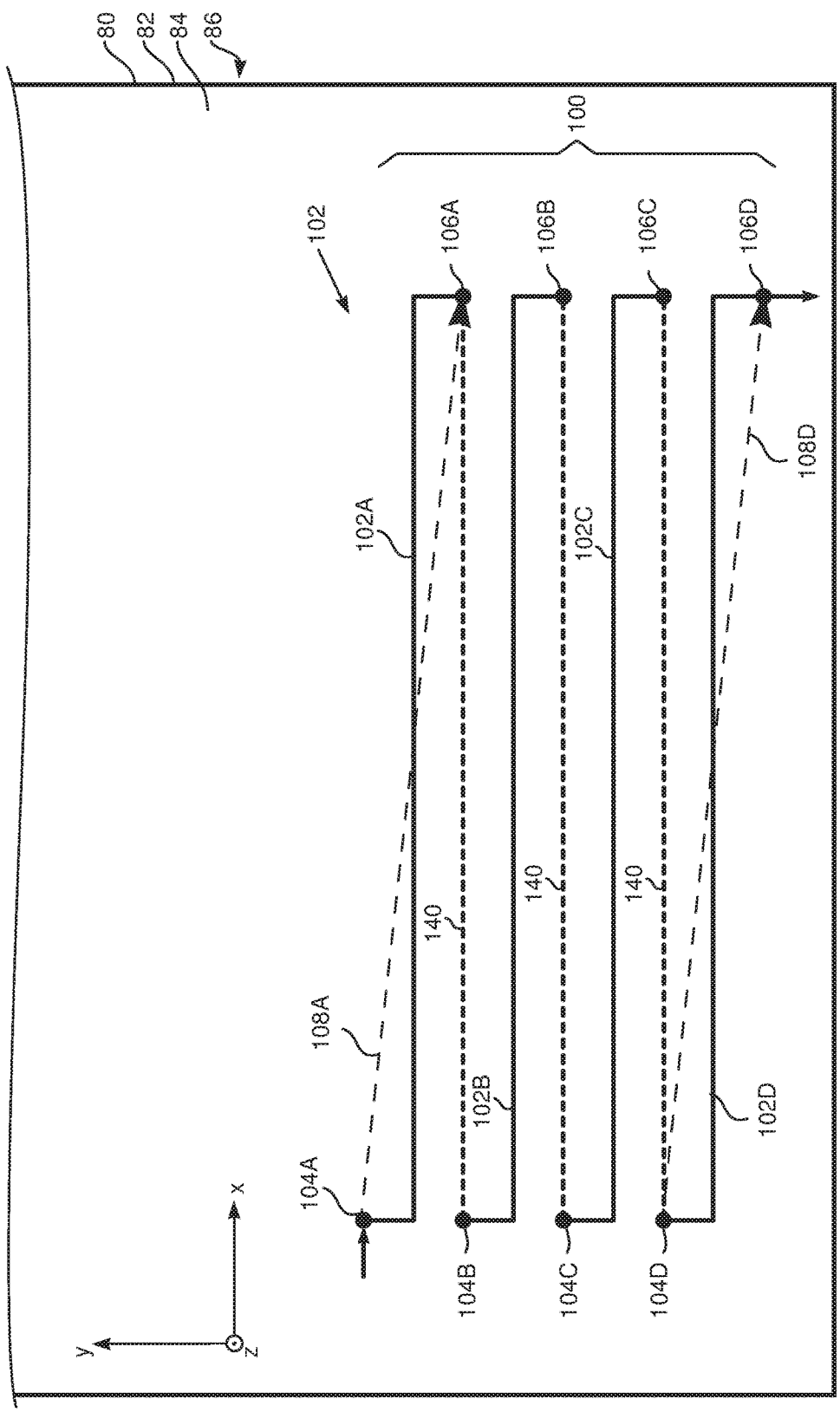

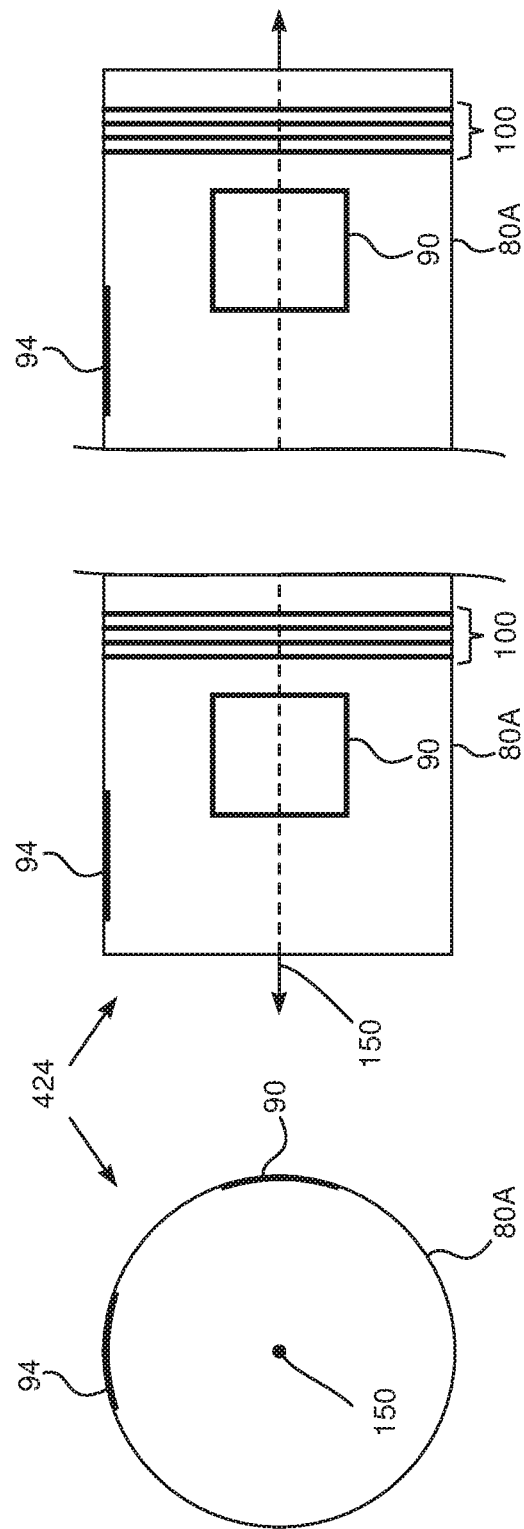

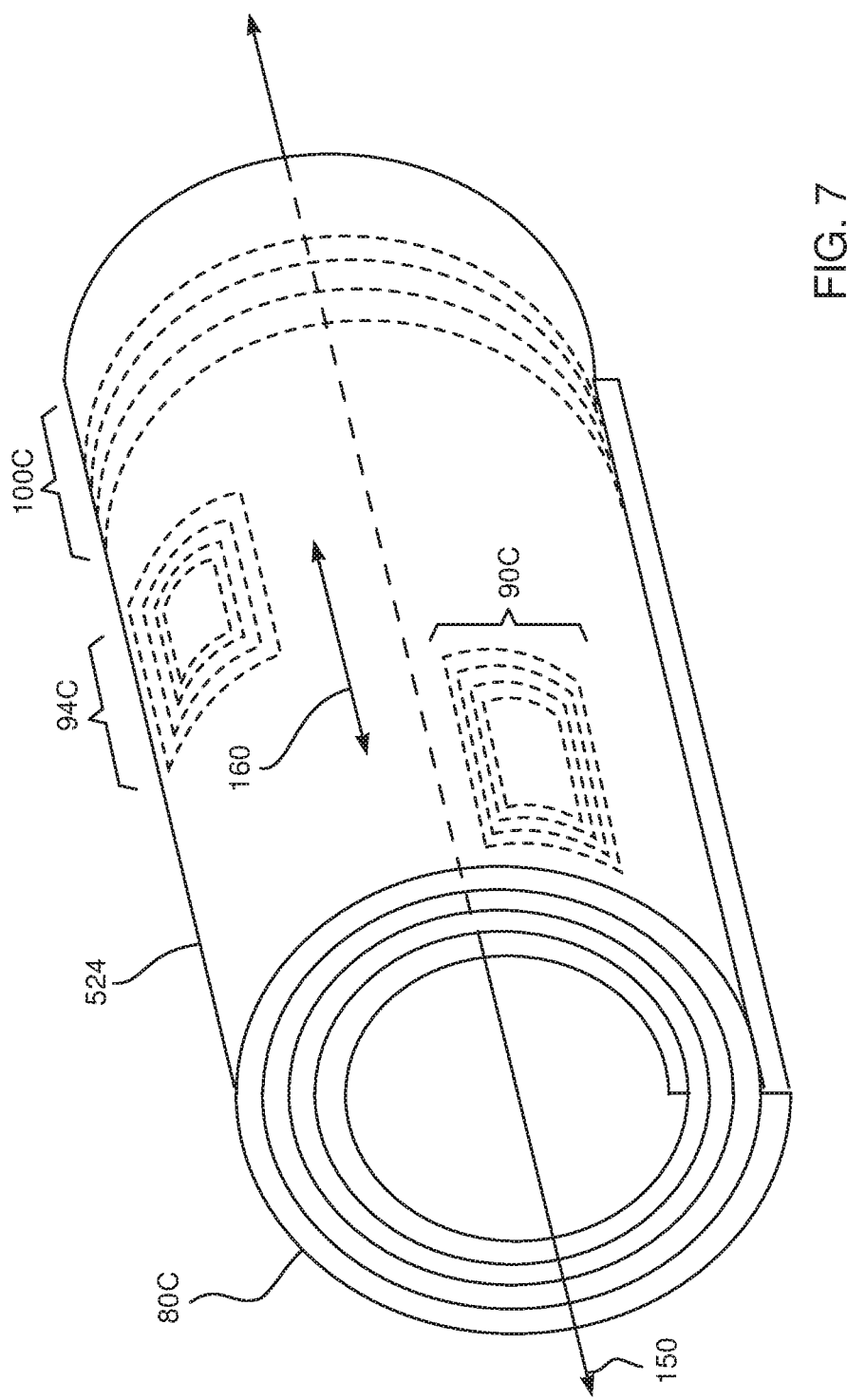

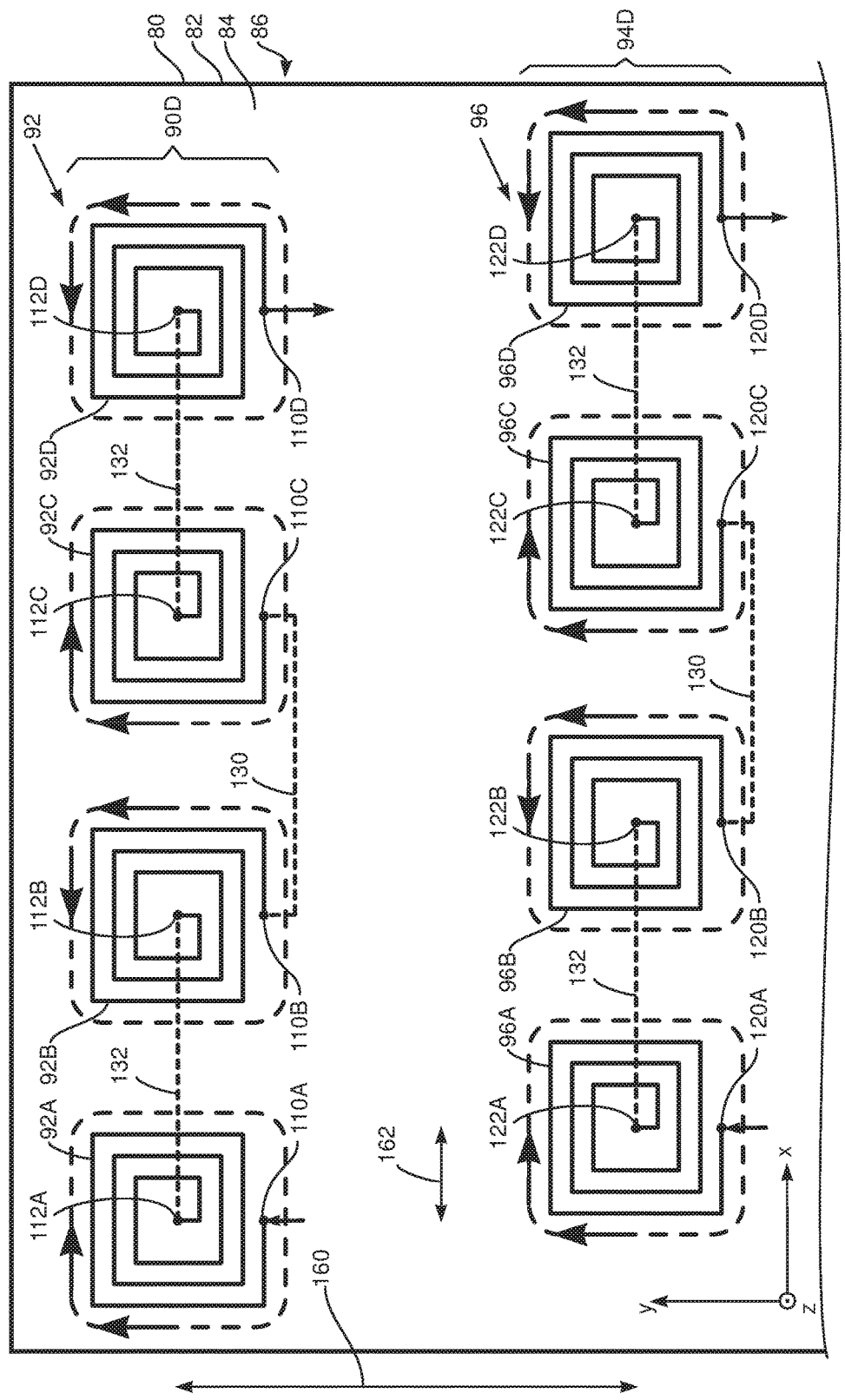

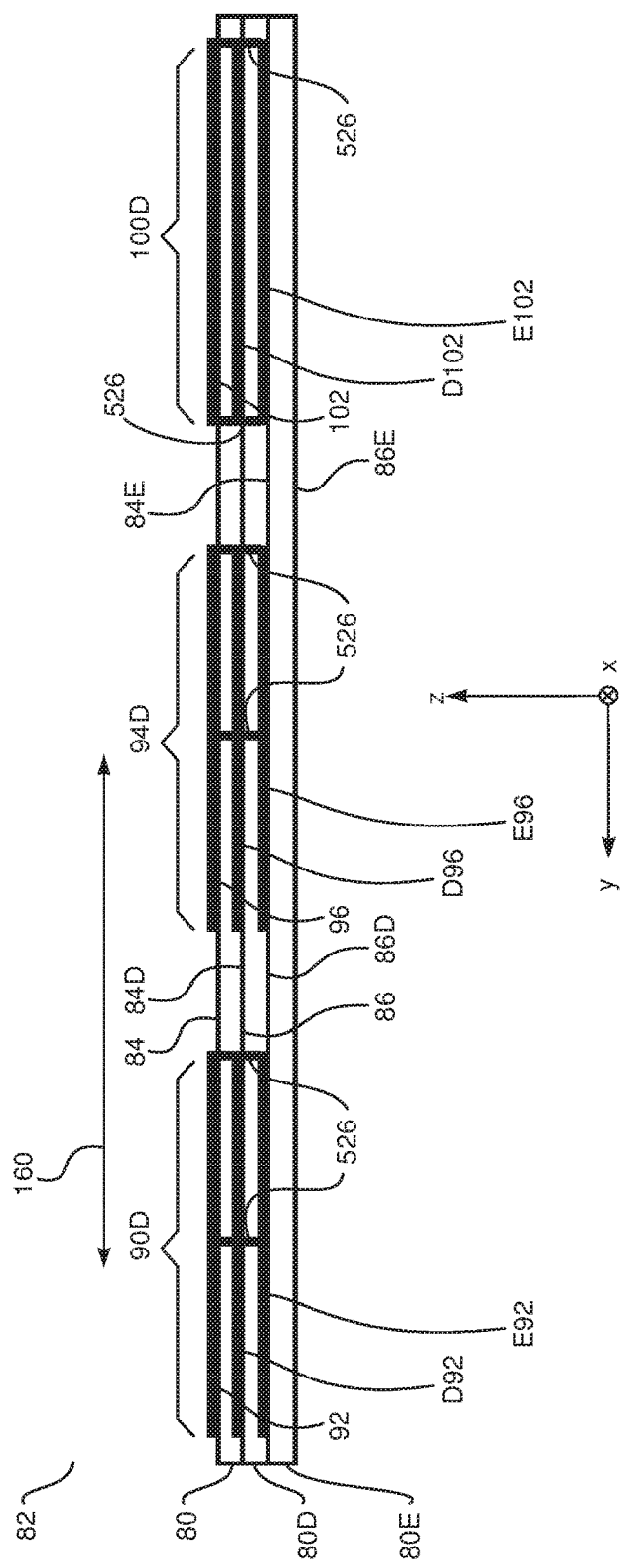

TRIPLE AXIS SENSOR ON A SINGLE LAYER PRINTED CIRCUIT

FIELD OF THE INVENTION

The present invention relates generally to circuitry, and specifically to circuitry formed on a printed circuit board.

BACKGROUND OF THE INVENTION

One of the methods for sensing magnetic fields is to position a coil so that it is traversed by the field. A potential induced in the coil provides a measure of the field traversing the coil.

U. S. Patent Application 2015/0303706, to Bronson et al. whose disclosure is incorporated herein by reference, describes a current sensing system for wireless energy transfer that may include a printed circuit board, wherein the printed circuit board may include at least a first layer, a second layer, and a third layer.

PCT Patent Application WO2016083839 to Foord, whose disclosure is incorporated herein by reference, describes a substrate comprising an aperture for receiving a sample of a substance to be tested. The substrate has an electrically conductive coil printed thereon, which surrounds the aperture.

U.S. Pat. No. 6,998,813, to Heizmann et al. whose disclosure is incorporated herein by reference, describes a supporting member of a tachogenerator. The supporting member is executed as a printed circuit board (PCB), whereby contacts are provided on one side of the PCB.

U.S. Pat. No. 7,518,374, to Olsson et al. whose disclosure is incorporated herein by reference, describes a portable locator for detecting a buried object characterized by an electromagnetic (EM) field emission employing three-dimensional sensor arrays each having three substantially-identical EM field sensors disposed on a flexible annular wall having a radial centroid defining a sensing axis.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:

a flexible insulating substrate, having a first side and a second side, rolled about an axis parallel to the substrate;

a first planar conducting spiral that is right-handed relative to a normal to the substrate, and a second planar conducting spiral that is left-handed relative to the normal, formed on the first side of the substrate, the first conducting spiral having a first initial termination and a first final termination, the second conducting spiral having a second initial termination and a second final termination, the spirals having a displacement therebetween, with a preset magnitude so that when the substrate is rolled about the axis the first initial termination aligns with the second initial termination; and a via penetrating the substrate from the first side to the second side so as to interconnect the first initial termination and the second initial termination.

Typically, at least one of the first and the second conducting spirals includes a rectilinear element. Alternatively or additionally, at least one of the first and the second conducting spirals includes a curvilinear element.

Typically, wherein when the substrate is rolled about the axis the first final termination aligns with the second final termination.

In a disclosed embodiment the first conducting spiral is a mirror image of the second conducting spiral.

In a further disclosed embodiment the apparatus includes:

a third planar conducting spiral that is right-handed relative to the normal to the substrate, formed on the first side of the substrate, and that includes a third initial termination and a third final termination, the third spiral having a further displacement from the second spiral so that when the substrate is rolled about the axis the second final termination aligns with the third final termination; and a second via penetrating the substrate from the first side to the second side so as to interconnect the second final termination and the third final termination.

In a yet further disclosed embodiment the apparatus includes:

a third planar conducting spiral that is right-handed relative to the normal to the substrate, and a fourth planar conducting spiral that is left-handed relative to the normal, formed on the first side of the substrate, the third conducting spiral having a third initial termination and a third final termination, the fourth conducting spiral having a fourth initial termination and a fourth final termination, the third and the fourth spirals having the displacement with the preset magnitude therebetween, and wherein a first line segment joining the third and the fourth spirals has a second displacement from a second line segment joining the first and the second spirals, and so that when the substrate is rolled about the axis the third initial termination aligns with the fourth initial termination; and a second via penetrating the substrate from the first side to the second side so as to interconnect the third initial termination and the fourth initial termination.

When the substrate is rolled about the axis an angle between a first line, from the first spiral to the axis, and a second line, from the third spiral to the axis, may be 90°.

When the substrate is rolled about the axis a first plane, containing a first line from the first spiral to the axis and orthogonal to the axis, may be disjoint from a second plane, containing a second line from the third spiral to the axis and orthogonal to the axis.

The second displacement may be parallel to the axis.

In a still yet further disclosed embodiment the apparatus includes:

a third planar conducting spiral that is right-handed relative to the normal to the substrate, and a fourth planar conducting spiral that is left-handed relative to the normal, formed on the first side of the substrate, the third conducting spiral having a third initial termination and a third final termination, the fourth conducting spiral having a fourth initial termination and a fourth final termination, the third and the fourth spirals having the displacement with the preset magnitude therebetween, and wherein the first, second, third, and fourth spirals lie on a common line segment, so that when the substrate is rolled about the axis the third initial termination aligns with the fourth initial termination of the fourth conducting spiral; and a second via penetrating the substrate from the first side to the second side so as to interconnect the third initial termination and the fourth initial termination.

When the substrate is rolled about the axis an angle between a first line, from the first spiral to the axis, and a second line, from the third spiral to the axis, may be 90°.

When the substrate is rolled about the axis parallel to the substrate the first and third spirals may lie in a common plane orthogonal to the axis parallel to the substrate.

In an alternative embodiment the apparatus includes:

one or more third planar conducting spirals having respective third initial terminations and third final terminations, the one or more third planar conducting spirals being right-handed relative to the normal to the substrate and being embedded therein so that the respective third initial terminations align with the first initial termination and so that the respective third final terminations align with the first final termination;

one or more second vias interconnecting the respective third initial terminations and the first initial termination; and one or more third vias interconnecting the respective third final terminations and the first final termination.

Typically, the flexible insulating substrate includes a first flexible insulating substrate, and the apparatus further includes:

a second flexible insulating substrate, having a third side and a fourth side abutting and overlaying the first side of the first flexible insulating substrate, rolled about the axis;

a third planar conducting spiral, that is right-handed relative to the normal, formed on the third side of the second substrate, the third conducting spiral having a third initial termination and a third final termination that respectively align with the first initial termination and the first final termination;

a second via penetrating the second substrate from the third side to the fourth side so as to interconnect the third initial termination and the first initial termination; and a third via penetrating the second substrate from the third side to the fourth side so as to interconnect the third final termination and the first final termination.

In a further alternative embodiment the apparatus includes a magnetic tracking system, and, when the substrate is rolled about the axis and the via interconnects the first and second initial terminations the first and second conducting spirals operate as a sensing coil in the magnetic tracking system.

There is further provided, according to an embodiment of the present invention apparatus, including:

a flexible insulating substrate, having a first side and a second side, rolled about an axis parallel to the substrate;

a first conducting line and a second conducting line formed on the first side of the substrate, the first conducting line having a first initial termination and a first final termination, the second conducting line having a second initial termination and a second final termination, the first line defining a first ray along the substrate from the first initial termination to the first final termination, the second line defining a second ray along the substrate from the second initial termination to the second final termination, the first and second rays having a common direction, the lines having a displacement therebetween, parallel to the axis, with a preset magnitude so that when the substrate is rolled about the axis the first final termination aligns with the second initial termination; and a via penetrating the substrate from the first side to the second side so as to interconnect the first final termination with the second initial termination.

At least one of the first and the second conducting lines may include a rectilinear element. Alternatively or additionally, at least one of the first and the second conducting lines may include a curvilinear element.

The apparatus may include:

a third conducting line and a fourth conducting line formed on the first side of the substrate, the third conducting line having a third initial termination and a third final termination, the fourth conducting line having a fourth initial termination and a fourth final termination, the third line defining a third ray along the substrate from the third initial termination to the third final termination, the fourth line defining a fourth ray along the substrate from the fourth initial termination line to the fourth final termination, the third and fourth rays having the common direction, the lines having the displacement, parallel to the axis, with the preset magnitude therebetween, so that when the substrate is rolled about the axis the third final termination aligns with the fourth initial termination, and so that the first and second lines define a first plane orthogonal to the axis, and the third and fourth planes define a second plane, distinct from the first plane, orthogonal to the axis; and a second via penetrating the substrate from the first side to the second side so as to interconnect the third final termination with the fourth initial termination.

The apparatus may include:

one or more third conducting lines having respective third initial terminations and third final terminations, the one or more third conducting lines being embedded in the substrate and defining respective one or more third rays from the respective third initial terminations to the respective final terminations therein, the one or more third rays having the common direction, so that the respective third initial terminations align with the first initial termination and so that the respective third final terminations align with the first final termination;

one or more second vias interconnecting the respective third initial terminations and the first initial termination; and one or more third vias interconnecting the respective third final terminations and the first final termination.

In a disclosed embodiment the flexible insulating substrate includes a first flexible insulating substrate, and the apparatus further includes:

a second flexible insulating substrate, having a third side and a fourth side abutting and overlaying the first side of the first flexible insulating substrate, rolled about the axis;

a third conducting line formed on the third side of the second substrate, the third conducting line having a third initial termination and a third final termination that respectively align with the first initial termination and the first final termination;

a second via penetrating the second substrate from the third side to the fourth side so as to interconnect the third initial termination and the first initial termination; and a third via penetrating the second substrate from the third side to the fourth side so as to interconnect the third final termination and the first final termination of the first line.

The apparatus may include a magnetic tracking system, and, when the substrate is rolled about the axis and the via interconnects the first final termination and the second initial termination the first and second conducting lines may operate as a sensing coil in the magnetic tracking system.

There is further provided, according to an embodiment of the present invention a method, including:

rolling a flexible insulating substrate, having a first side and a second side, about an axis parallel to the substrate;

forming a first planar conducting spiral that is right-handed relative to a normal to the substrate, and a second planar conducting spiral that is left-handed relative to the normal, on the first side of the substrate, the first conducting spiral having a first initial termination and a first final termination, the second conducting spiral having a second initial termination and a second final termination, the spirals having a displacement therebetween, with a preset magnitude so that when the substrate is rolled about the axis the first initial termination aligns with the second initial termination; and penetrating the substrate with a via from the first side to the second side so as to interconnect the first initial termination and the second initial termination.

There is further provided, according to an embodiment of the present invention, a method, including:

rolling a flexible insulating substrate, having a first side and a second side, about an axis parallel to the substrate;

forming on the first side of the substrate a first conducting line and a second conducting line, the first conducting line having a first initial termination and a first final termination, the second conducting line having a second initial termination and a second final termination, the first line defining a first ray along the substrate from the first initial termination to the first final termination, the second line defining a second ray along the substrate from the second initial termination to the second final termination, the first and second rays having a common direction, the lines having a displacement therebetween, parallel to the axis, with a preset magnitude so that when the substrate is rolled about the axis the first final termination aligns with the second initial termination; and penetrating the substrate with a via from the first side to the second side so as to interconnect the first final termination with the second initial termination.

The present disclosure will be more fully understood from the following detailed description of the embodiments thereof, taken together with the drawings, in which:

BRIEF DESCRIPTION OF THE DRAWINGS

FIGS. 2A, 2B, and 2C are schematic diagrams illustrating a flexible sheet used to produce a sensor.

FIG. 5D is a schematic depiction of a plurality of sensors, according to an embodiment of the present invention;

FIG. 7 is a schematic diagram illustrating how the sheet is rolled up to form the sensor, according to an embodiment of the present invention;

FIGS. 8A, 8B, and 8C are schematic diagrams illustrating flexible sheets used to produce a sensor.

DETAILED DESCRIPTION OF EMBODIMENTS

Overview

Figure 1:
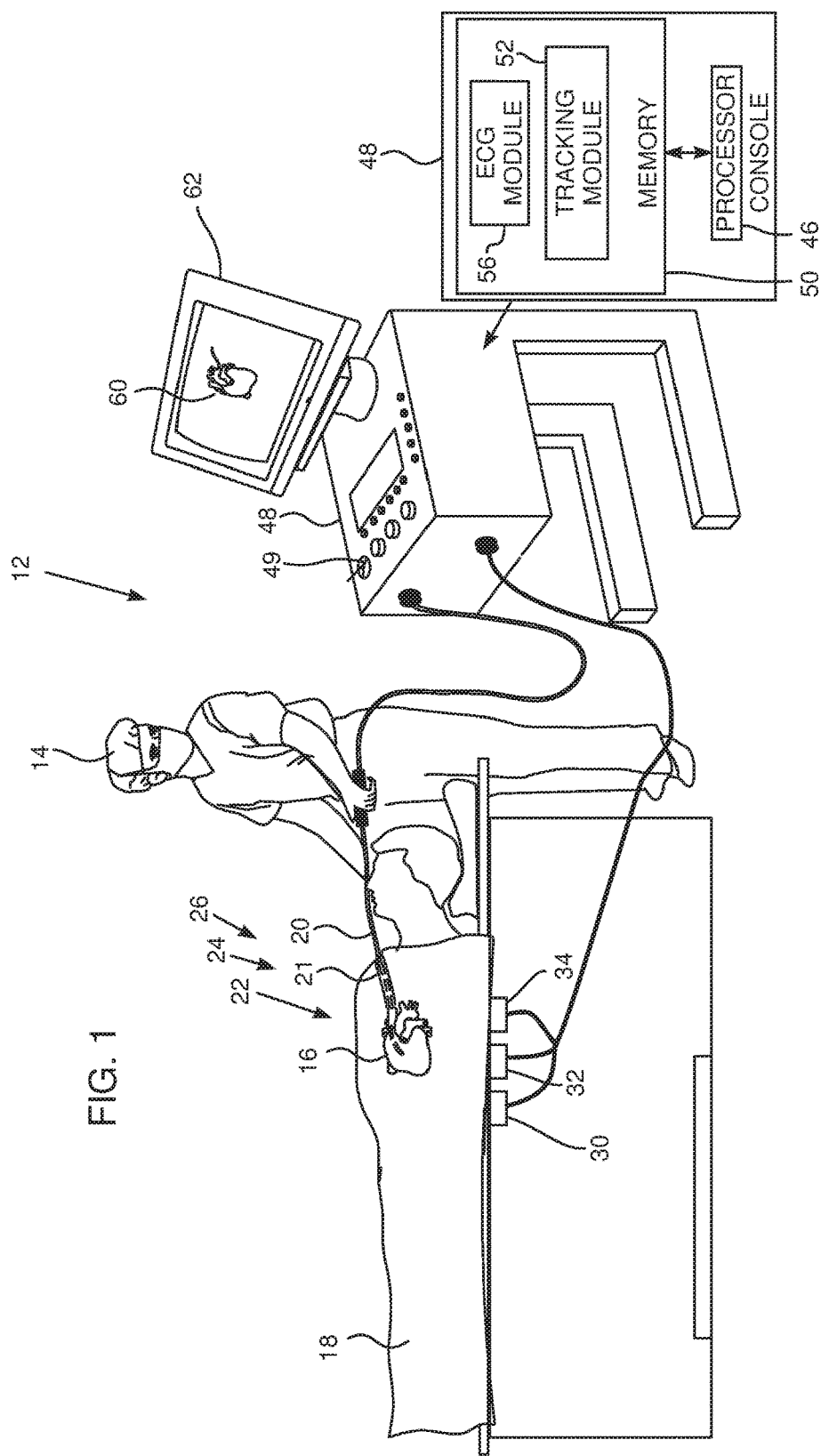
FIG. 1 is a schematic illustration of an invasive medical procedure, according to an embodiment of the present invention.

Embodiments of the present invention provide a system for forming coils, the coils typically comprising three coils that are mutually orthogonal to each other, on flexible printed circuit board (PCB). The PCB comprises an insulating substrate having a first and a second side, and conducting elements of the coils are formed on only one of the sides, so that the PCB is also termed a single-sided PCB. In order to form the coils the flexible single-sided PCB is rolled up, in a Swiss roll configuration, so that conducting elements formed on the one side align. The elements are then connected by vias penetrating the substrate, the connected elements forming the coils.

In one embodiment a flexible insulating substrate, having a first side and a second side, is rolled about an axis parallel to the substrate. Prior to the rolling, a first planar conducting spiral that is right-handed relative to a normal to the substrate, and a second planar conducting spiral that is left-handed relative to the normal, is formed on the first side of the substrate.

The first conducting spiral has a first initial termination and a first final termination, and the second conducting spiral has a second initial termination and a second final termination. There is a displacement with a preset magnitude between the spirals, so that when the substrate is rolled about the axis the first initial termination aligns with the second initial termination.

A conductive via penetrates the substrate from the first side to the second side so as to interconnect the first initial termination and the second initial termination of the two spirals.

Forming a set of three mutually orthogonal coils from a single-sided PCB significantly reduces the cost of preparing such coils, compared to prior art systems for producing the coils.

System Description

In the following description, like elements in the drawings are identified by like numerals, and the like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise an electropotential investigation of a portion of a myocardium 16 of the heart of a human patient 18. However, it will be understood that embodiments of the present invention are not just applicable to this specific procedure, and may include substantially any procedure on biological tissue or on non-biological material.

In order to perform the investigation, professional 14 inserts a probe 20 into a sheath 21 that has been pre-positioned in a lumen of the patient. Sheath 21 is positioned so that a distal end 22 of the probe enters the heart of the patient. Distal end 22 comprises a position sensor 24, described in more detail below, that enables the location and orientation of the distal end to be tracked. Distal end 22 also comprises an electrode 26 which is used to acquire electropotentials of myocardium 16.

Sensor 24 comprises a plurality of coils. While the description herein describes using the coils for sensing magnetic fields, it will be understood that the coils may also be used to produce magnetic fields.

Apparatus 12 is controlled by a system processor 46, which is located in an operating console 48 of the apparatus. Console 48 comprises controls 49 which are used by professional 14 to communicate with the processor. The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 that is displayed on a screen 62.

In order to operate apparatus 12, processor 46 communicates with a memory 50, which has a number of modules used by the processor to operate the apparatus. Thus, memory 50 comprises an electrocardiograph (ECG) module 56 which acquires and analyzes signals from electrode 26. Memory 50 also comprises a tracking module 52, which receives signals from sensor 24, and which analyzes the signals in order to generate the location and orientation of distal end 24. Modules 56 and 54 may comprise hardware and/or software components. Memory 50 typically comprises other modules, such as a force module for measuring the force on end 24, and an irrigation module allowing the processor to control irrigation provided for distal end 22. For simplicity, such other modules are not illustrated in FIG. 1.

In addition to receiving and analyzing signals from sensor 24, tracking module 52 also controls radiators 30 32, and 34. The radiators are positioned in proximity to myocardium 16, and are configured to radiate alternating magnetic fields into a region in proximity to the myocardium. As is explained below, sensor 24 comprises three orthogonal coils, and each of the coils generate signals in response to the radiated magnetic fields traversing the coils; it is these signals that are received and analyzed by module 52, so enabling processor 46 to track distal end 22. The Carto® system produced by Biosense Webster, of Diamond Bar, CA, uses such a magnetic tracking system.

Figure 2A:
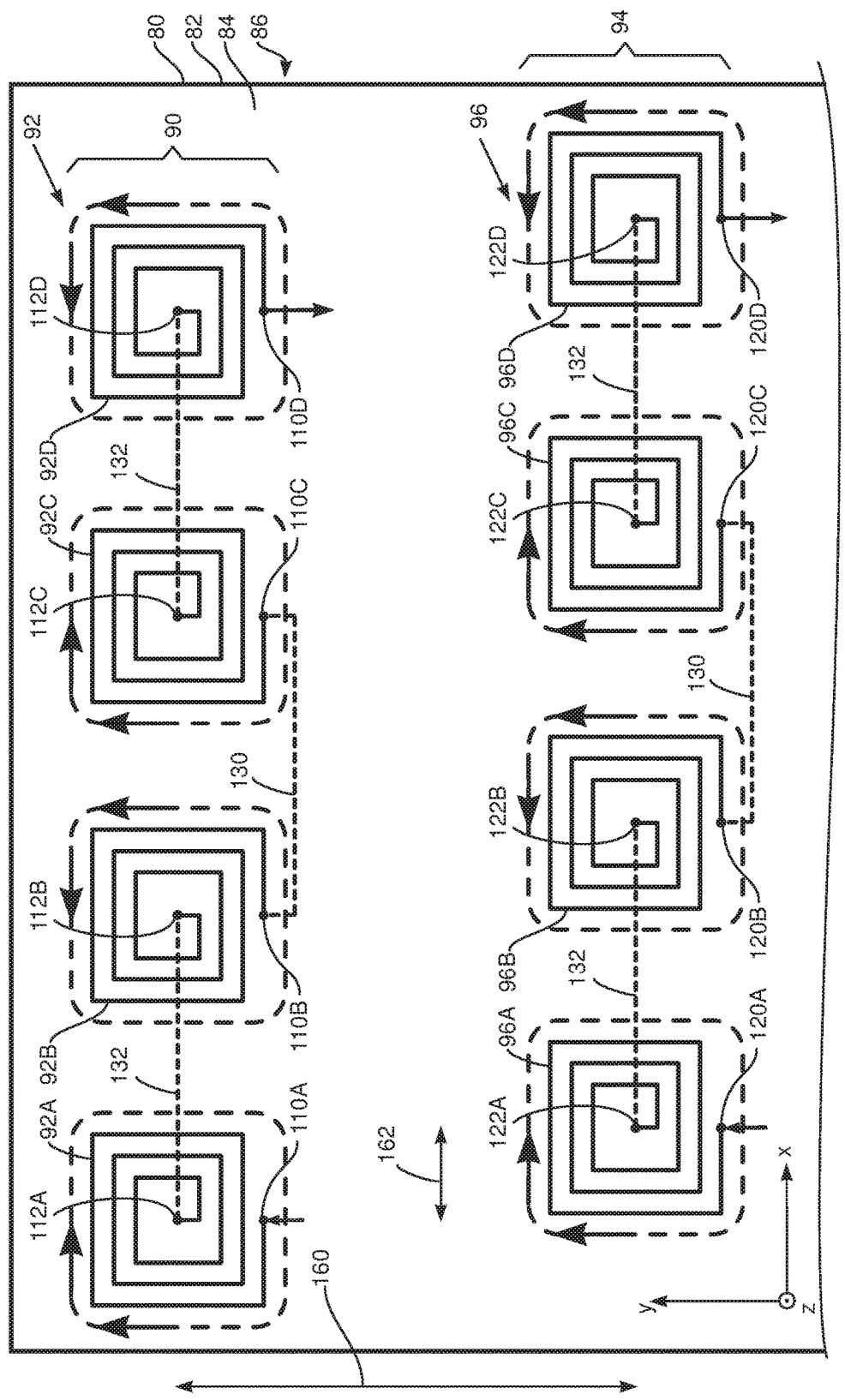
Figure 2C:
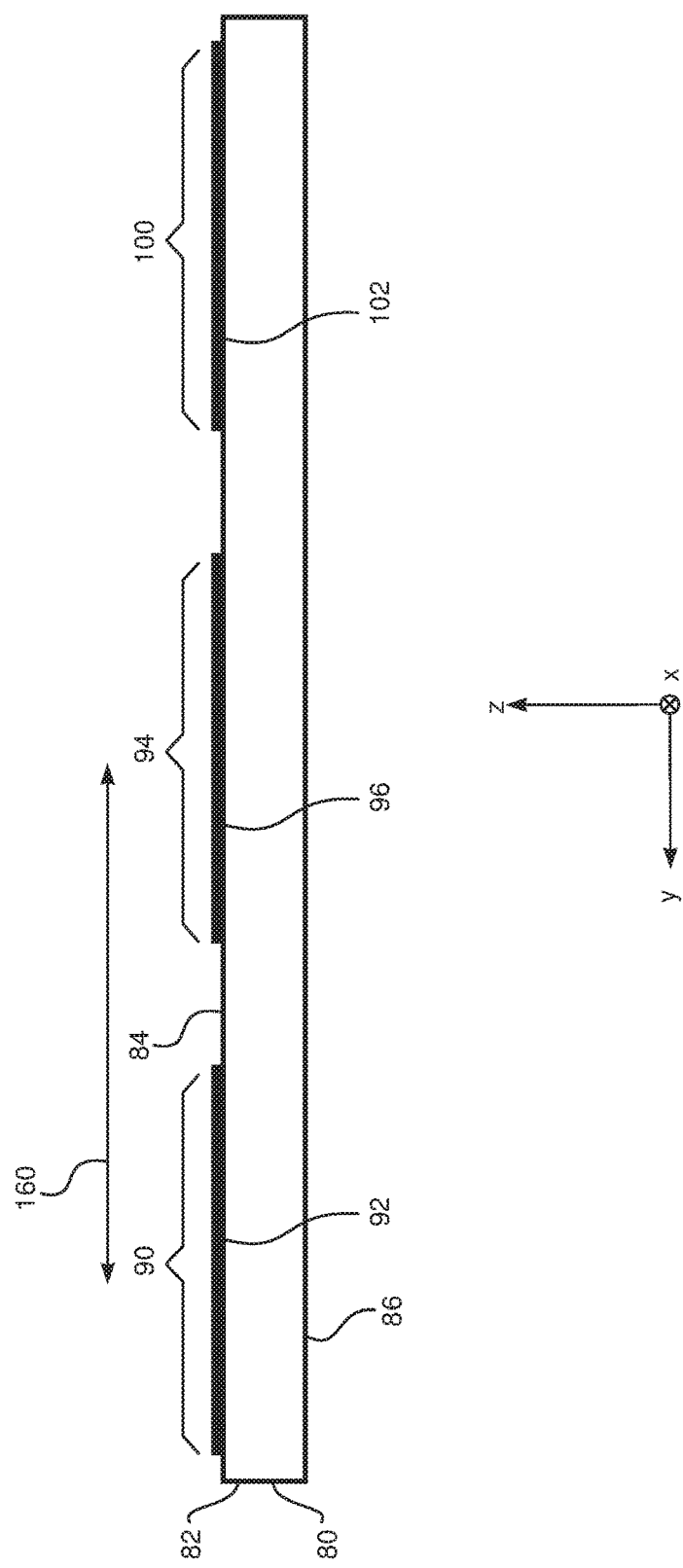
Figure 3:
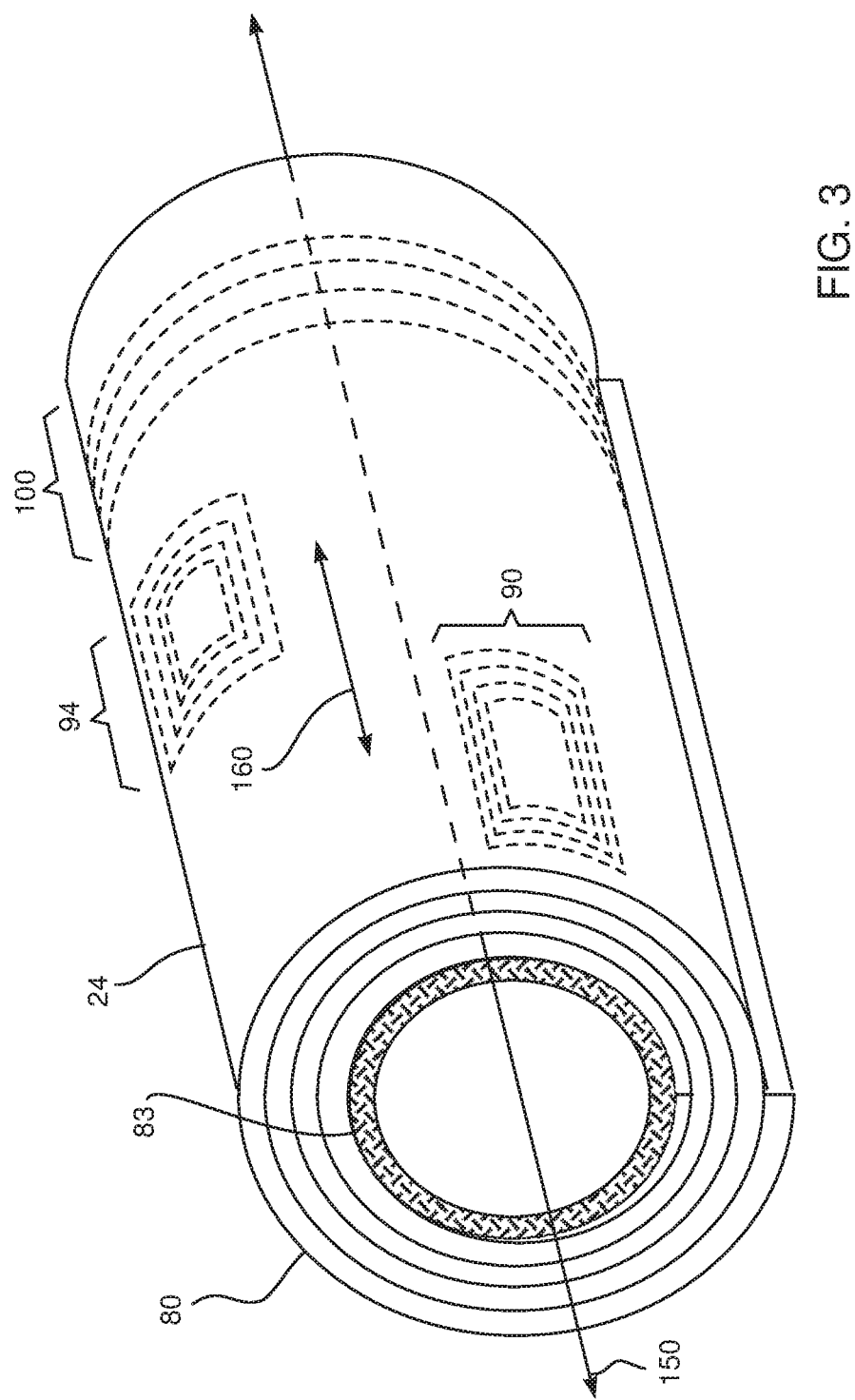
FIGS. 3, 4A, 4B are schematic diagrams illustrating how the sheet is rolled up to form the sensor, according to an embodiment of the present invention.
Figure 4B:
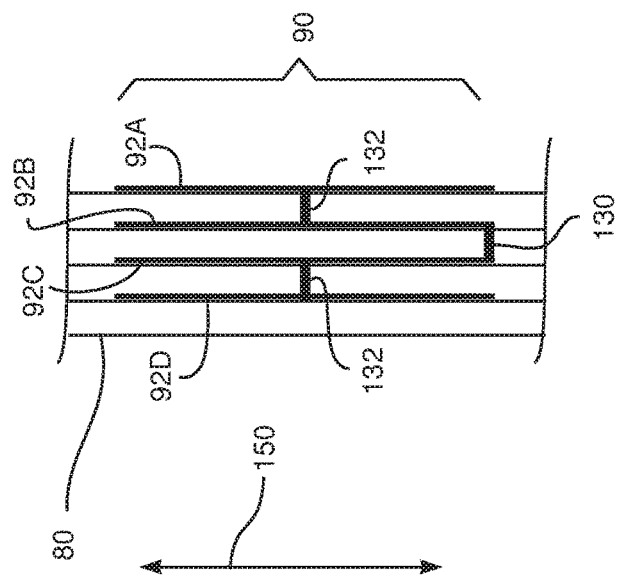
Figure 4A:
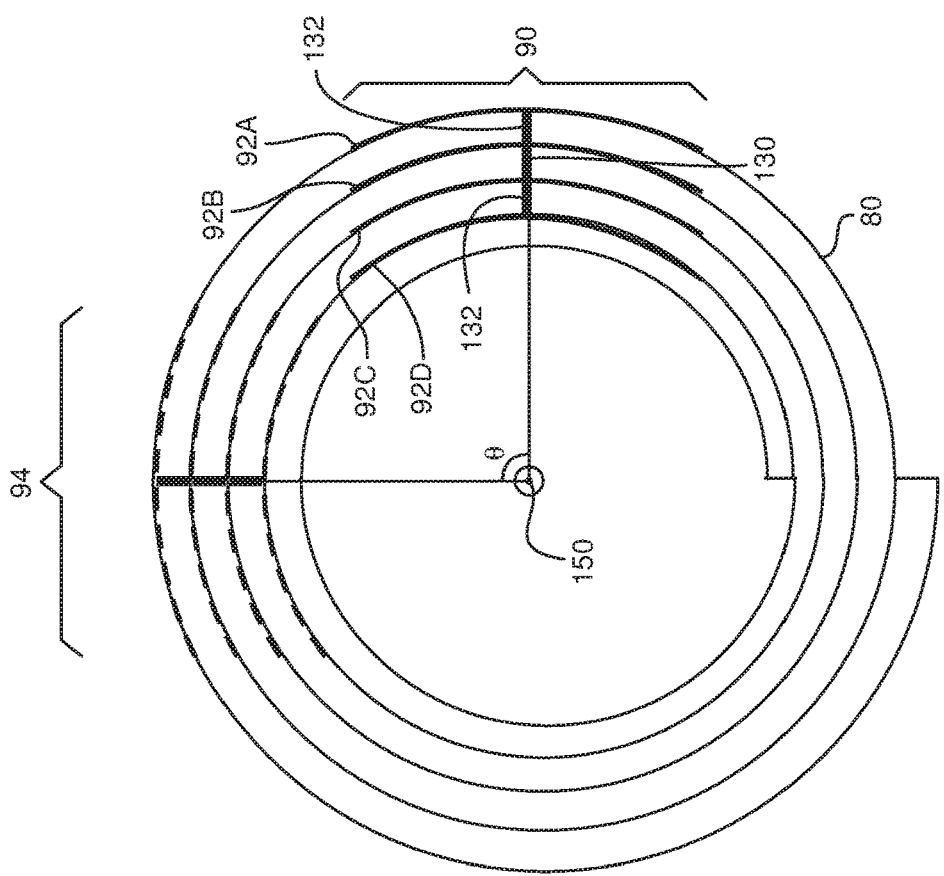

FIGS. 2A, 2B, and 2C are schematic diagrams illustrating a flexible sheet 80 used to produce sensor 24, and FIGS. 3, 4A, 4B are schematic diagrams illustrating how the sheet is rolled up to form the sensor, according to an embodiment of the present invention. FIG. 2A illustrates a top portion of sheet 80, and FIG. 2B illustrates a bottom portion of the sheet, both figures being viewed from above the sheet. FIG. 2C is a side view of sheet 80. FIG. 3 is a schematic perspective view of the formed sensor, FIG. 4A is a schematic cross-section of the sensor as viewed along an axis of the sensor, and FIG. 4B is a schematic cross-section of a portion of the sensor as viewed orthogonal to the sensor axis.

Referring to FIGS. 2A, 2B, and 2C, sheet 80 comprises a flexible insulating, substantially two-dimensional (2D), substrate 82, having a first side 84 and a second side 86. In one embodiment substrate 82 is formed from a polyimide material, but other embodiments may comprise any convenient flexible insulating material. In producing sensor 24, sheet 80 is typically initially clad with conducting material, typically copper, on first side 84, while second side 86 does not have any conducting cladding. Thus, in the following description side 84 is also referred to as conducting side 84, and side 86 is also referred to as non-conducting side 86.

For clarity in the description of sheet 80, the sheet is assumed to be referenced to a set of xyz orthogonal axes, wherein the sheet lies in an xy plane, and there is a z axis normal to the sheet. In FIGS. 2A and 2B the z axis is assumed to be directed out of the plane of the paper.

On the conducting side three sets of conducting elements are formed. The conducting elements are rectilinear, i.e., all parts of the element are straight lines which are in one of two orthogonal directions. The directions are herein assumed to be parallel to the x axis or the y axis. A first set 90 of conducting elements comprises a first plurality of spiral conductors 92. By way of example, FIG. 2A illustrates four spiral conductors, identified as spiral conductors 92A, 92B, 92C, 92D. A second set 94 comprises a second plurality of spiral conductors 96, illustrated by way of example as spiral conductors 96A, 96B, 96C, 96D. A third set 100, illustrated in FIG. 2B, comprises a third set of conductive lines 102, and in FIG. 2B there are by way example four lines 102A, 102B, 102C, and 102D.

The spirals of first set 90 are positioned along a line segment parallel to the x-axis, and except as described below the spirals are generally similar. Each spiral of set 90 has an initial termination 110 and a final termination 112, so that the four example spirals in the figure have initial terminations 110A, 110B, 110C, 110D and final terminations 112A, 112B, 112C, 112D. Adjacent spirals are typically mirror images, in a yz mirror plane centered between the spirals, so that the spirals alternate between rotating in a right handed direction around a normal to sheet 80 and in a left handed direction about the normal. Thus, as illustrated by the arrows around the spirals in FIG. 2A, spiral conductors 92A, 92C rotate in a right handed direction, and spiral conductors 92B, 92D rotate in a left handed direction.

As stated above the spirals of set 90 are positioned along a line segment parallel to the x-axis. Furthermore, the spirals are separated from each other along the line segment, and the separations are such that when sheet 80 is rolled about itself, around an axis 150 parallel to the y-axis that is herein also termed the sensor axis, the spirals of set 90 align with themselves, as is illustrated schematically in FIG. 3. In addition, initial terminations 110A, 110B, 110C, 110D align with themselves, and final terminations 112A, 112B, 112C, 112D also align with themselves. Typically the separation of adjacent spirals on conducting side 84 is approximately constant, but differs because as sheet 80 rolls about itself, the distance of the sheet from the sheet axis increases.

In forming sensor 24 by rolling sheet 80 about itself, the sheet may be rolled about a former 83 as illustrated in FIG. 3. In an alternative embodiment, the sheet is rolled about itself, so there is no former present in sensor 24. For simplicity, in other diagrams of the present disclosure, former 83 is not shown. In one embodiment, sensor 24 is approximately cylindrical, having a diameter of approximately 2-5 mm and a length of approximately 5-10 mm.

In the rolled up configuration described above sheet 80 is in a configuration termed a Swiss roll configuration. In the Swiss roll configuration, for any given spiral in set 90 except the "end" spirals, a first conductive via 130 penetrates through the first side of sheet 80 to the second side of the sheet to interconnect the initial termination of the given spiral with the initial termination of a spiral immediately above the given spiral. In addition a second conductive via 132 penetrates through the first side of sheet 80 to the second side of the sheet to interconnect the final termination of the given spiral with the final termination of a spiral immediately below the given spiral. In FIG. 2A vias 130, 132 are shown as broken lines.

FIG. 4A is a schematic cross-section of sensor 24, taken in a plane orthogonal to sensor axis 150, and FIG. 4B is a schematic cross-section of set 90 of the sensor, taken in a plane parallel to axis 150. FIGS. 4A and 4B illustrate the positioning of vias 130 and 132 as they interconnect spirals 92A, 92B, 92C, and 92D. In FIG. 2A spirals 92A and 92D are the end spirals of set 90. Thus, a first via 130 connects initial terminations 110B and 110C of spirals 92B, 92C, a second via 132 connects final terminations 112C and 112D, and a second via 132 connects final terminations 112A and 112B. As is shown in FIG. 2A, the end spirals are only connected to one other spiral by one termination of the end spiral and a via, and the other termination of the end spiral is not connected to any spiral.

Except for the following differences, the spirals of second set 94 are generally similar in layout and configuration to the spirals of first set 90. Thus, each spiral of set 94 has an initial termination 120 and a final termination 122, so that the four example spirals in the figure have initial terminations 120A, 120B, 120C, 120D and final terminations 122A, 122B, 122C, 122D. As for set 90, in set 94 adjacent spirals are typically mirror images, in a yz mirror plane centered between the spirals, so that the spirals alternate between rotating in a right handed direction around a normal to sheet 80 and in a left handed direction about the normal.

The spirals of set 94 are also positioned along a line segment parallel to the x-axis, and the spirals have substantially the same separations on the line segment as the spirals of set 90. In the rolled up configuration described above, the spirals of set 94 are also connected, by vias 130 and 132, substantially as described above for set 90. However the line segment for set 94 is displaced relative to the line segment of set 90. The displacement is in both the x and the y directions. A y displacement 160 causes set 94 to be displaced, with respect to set 90, parallel to the sheet axis. y displacement 160 is illustrated in FIGS. 2A and 2C, and in FIG. 3. An x displacement 162 is selected so that in sensor 24, an angle θ subtended by sets 90 and 94 to axis 150 is 90°. x displacement 162 is illustrated in FIG. 2A, and the corresponding angle θ is illustrated in FIG. 4A.

As illustrated in FIG. 2B, and as stated above, third set 100 of conducting elements comprises a plurality of conducting lines 102, and except for their terminations, the lines are typically parallel to the x axis and typically have equal lengths. The lines are displaced along the y axis relative to each other. Each line has an initial termination and a final termination, both of which are offset in the y direction from their respective line. Thus, the four example lines 102A, 102B, 102C, and 102D in the figure have initial terminations 104A, 104B, 104C, 104D and final terminations 106A, 106B, 106C, 106D respectively.

Each conducting line 102 defines a ray on first side of the substrate extending from its initial termination to its final termination, and the lines are laid out on surface 84 so that the rays of each line have a common direction. FIG. 2B illustrates two rays having the common direction, a first ray 108A from initial termination 104A to final termination 106A for line 102A, and a second ray 108D from initial termination 104D to final termination 106D for line 102D.

In addition, the conducting lines of set 100 are displaced relative to each other, parallel to the y axis, so that in the rolled up configuration described above the initial termination of a given line 102 aligns with the final termination of a neighboring line 102. This alignment applies except for the initial termination of a "first" line of set 100 and for the final termination of a "last" line of the set, which are not aligned with any terminations.

In the rolled up configuration, each pair of aligned terminations in set 100 is connected by a respective conductive via 140 which penetrates through the first side of sheet 80 to the second side of the sheet to interconnect the initial termination of a given line with the final termination of a neighboring line. Vias 140 are illustrated in FIG. 2B as broken lines.

Once sensor 24 has been formed, by sheet 80 being rolled up and the separate sets of spirals and lines connected by vias as described above, it will be understood that there are three orthogonal coils formed in the sensor, as is illustrated in FIG. 3. Each set 90, 94, and 100 forms a respective coil, and each of the coils has two "free" terminations, i.e., terminations that are not connected to any other termination of the set. Thus the coil of set 90 has free terminations 110A and 110D, the coil of set 94 has free terminations 120A and 120D, and the coil of set 100 has free terminations 104A and 106D.

If current is input to one of the free terminations of a coil it exits from the other free termination, as is illustrated by the arrows at terminations 110A and 110D, 120A and 120D, and 104A and 106D (FIGS. 2A, 2B). For each set (spirals or lines) the current traverses all the elements of the set in a common direction. Each coil of sensor 24 thus operates, in response to an alternating magnetic field traversing the coil, in the same way as a coil of wire in the field, generating an alternating potential between the two free terminations of the coil. Thus, via connected sets 90. 94, and 100 behave as respective coils of wire, so that in the via connected state the sets are also referred to herein as coils.

Figure 5A:
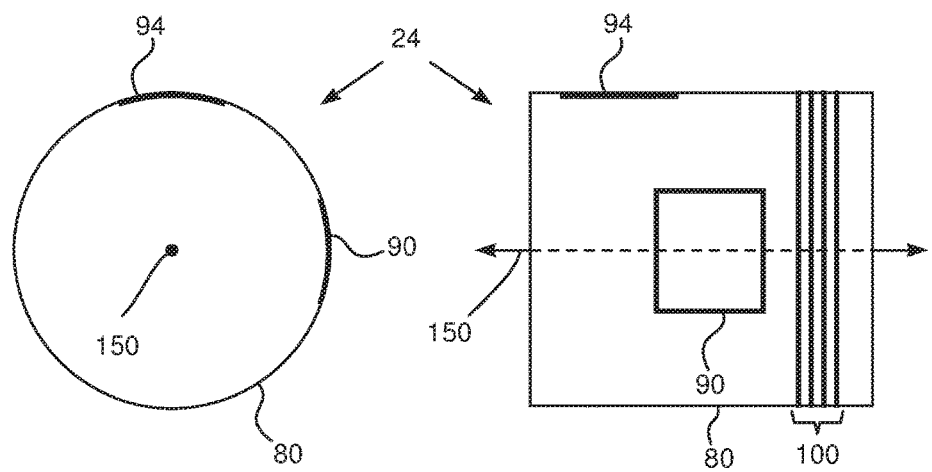
FIG. 5A is a schematic alternative depiction of the sensor, according to an embodiment of the present invention.

FIG. 5A is a schematic alternative depiction of sensor 24, according to an embodiment of the present invention. The depiction shows an end view of the sensor viewed along sensor axis 150, and a side view of the sensor viewed orthogonal to the sensor axis. In the end view rolled up sheet 80 is shown as a circle, and sets 90, 94 are shown as arcs on the circle. In the side view sheet 80 is shown as a rectangle, sets 94 and 100 are lines on or in the rectangle, and set 90 is also shown as a rectangle.

Figure 5B:
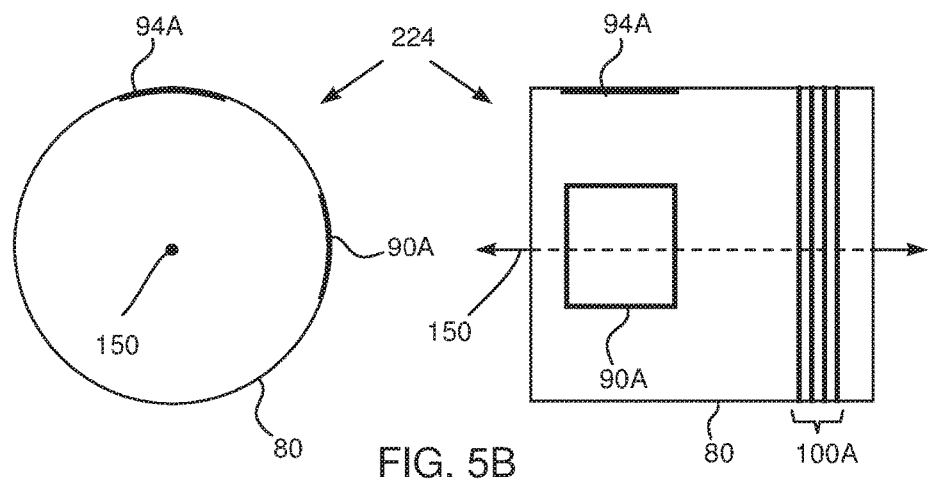
FIG. 5B is a schematic depiction of an alternative sensor, according to an embodiment of the present invention.

FIG. 5B is a schematic depiction of a sensor 224, according to an embodiment of the present invention. The depiction of sensor 224 is similar to that of sensor 24 in FIG. 5A. Apart from the differences described below, the operation of sensor 224 is generally similar to that of sensor 24 (FIGS. 1-5A), and elements indicated by the same reference numerals in both sensors 24 and 224 are generally similar in construction and in operation.

In sensor 224 a set of conducting elements 100A is generally similar in construction to set 100, as described above with respect to FIG. 2B and FIG. 3. However, in sensor 224, while sets 94A and 90A correspond respectively in operation to sets 94 and 90 of sensor 24, the construction of sets 94A and 90A is different from that of sets 94 and 90.

As is illustrated in the side view, sets 94A and 90A lie in a common plane that is orthogonal to sensor axis 150, whereas sets 94 and 90 lie in different disjoint planes orthogonal to the sensor axis. Thus, in constructing sensor 224, rather than sets 94A and 90A lying on different line segments parallel to the x-axis (FIG. 2A) on sheet 80 in its unrolled up state, the two sets of spirals lie on a common straight line segment. On the common line segment, the different spirals of the two sets are interleaved, and are located on the line segment so that when sheet 80 is rolled up, the spirals of set 94A overlap and alternate in rotation direction. Similarly, the spirals of set 90A overlap and alternate in rotation direction. Both sets of spirals are connected by vias as described above with respect to FIG. 2A.

Figure 5C:
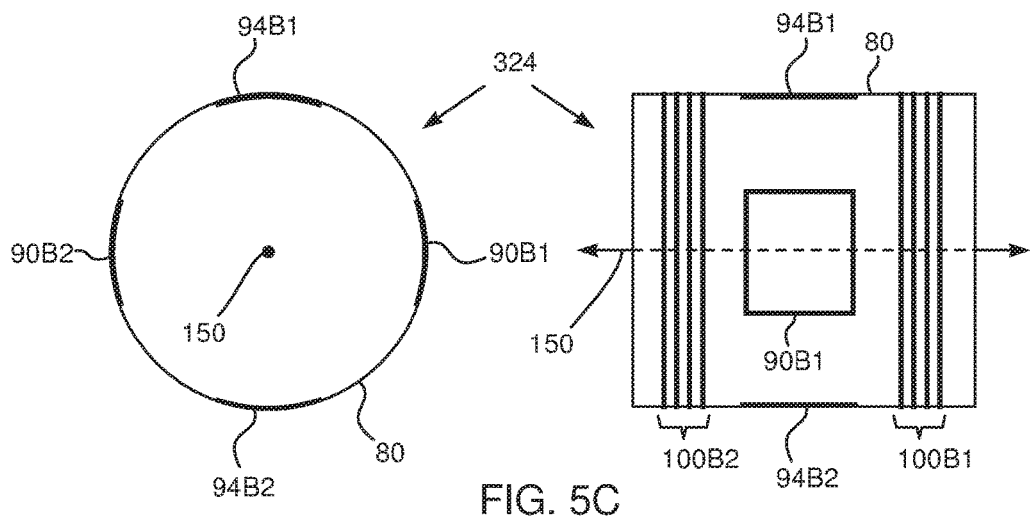
FIG. 5C is a schematic depiction of a further alternative sensor, according to an embodiment of the present invention.

FIG. 5C is a schematic depiction of a sensor 324, according to an embodiment of the present invention. The depiction of sensor 324 is similar to that of sensor 24 in FIG. 5A. Apart from the differences described below, the operation of sensor 324 is generally similar to that of sensor 224 (FIGS. 1-5A, 5B), and elements indicated by the same reference numerals in both sensors 224 and 324 are generally similar in construction and in operation.

In contrast to sensor 224 which has three coils that are orthogonal to each other, sensor 324 comprises three pairs of similar coils, the coils in a given pair having a common axis of symmetry and being separated along the axis. The three axes of the three pairs are orthogonal to each other. Thus, in sensor 324 each of a pair of conducting coils 100B1, 100B2 is generally similar to set 100A (FIG. 5B), the pair having a common axis of symmetry coincident with sensor axis 150, each of the coils in the pair defining a respective plane orthogonal to the axis, the planes being separated along the axis. In sensor 324 each of a pair of conducting coils 94B1, 94B2 is generally similar to set 94A, the pair having a common axis of symmetry orthogonal to, and intersecting, sensor axis 150, and being separated along the axis. Also in sensor 324, each of a pair of conducting coils 90B1, 90B2 is generally similar to set 90A (FIG. 5B), the pair having a common axis of symmetry orthogonal to sensor axis 150 and to the axis of coils 94B1, 94B2, and being separated along the axis.

When used as a magnetic field generator rather than as a sensor, each pair in sensor 324 may be configured to act as a Helmholtz pair of coils, so that at the intersection of the three axes of symmetry there is a region of nearly uniform magnetic field.

FIG. 5D is a schematic depiction of a plurality of sensors 424, according to an embodiment of the present invention. The depiction of sensors 424 is similar to that of sensor 24 in FIG. 5A. Apart from the differences described below, the operation of sensors 424 is generally similar to that of sensor 24 (FIGS. 1-5A), and elements indicated by the same reference numerals in both sensors 24 and 424 are generally similar in construction and in operation.

In contrast to sensor 24, which comprises one set of orthogonal coils, sensors 424 comprise two or more sets of orthogonal coils. Each set is substantially similar to sensor 24. However, sensors 424 are constructed on a single sheet 80A, which has substantially the same properties as sheet 80 (described above). However, a length of sheet 80A, measured along a line parallel to the y axis, which is parallel, as explained above, to sensor axis 150, is typically larger than that of sheet 80, and the length is selected so as to accommodate the plurality of orthogonal sensors on sheet 80A.

Figure 6A:
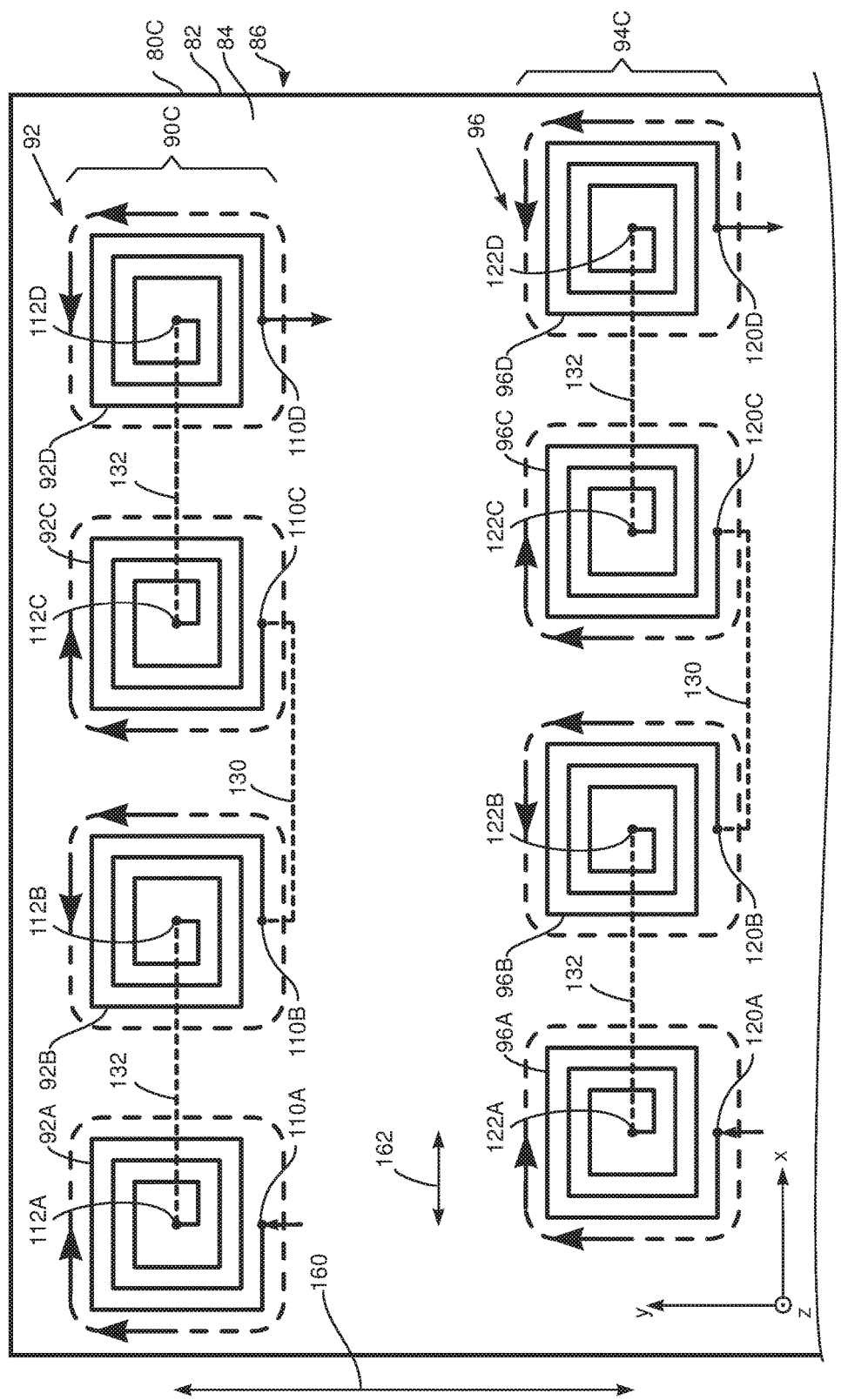
FIGS. 6A, 6B, and 6C are schematic diagrams illustrating a flexible sheet used to produce a sensor.
Figure 6B:
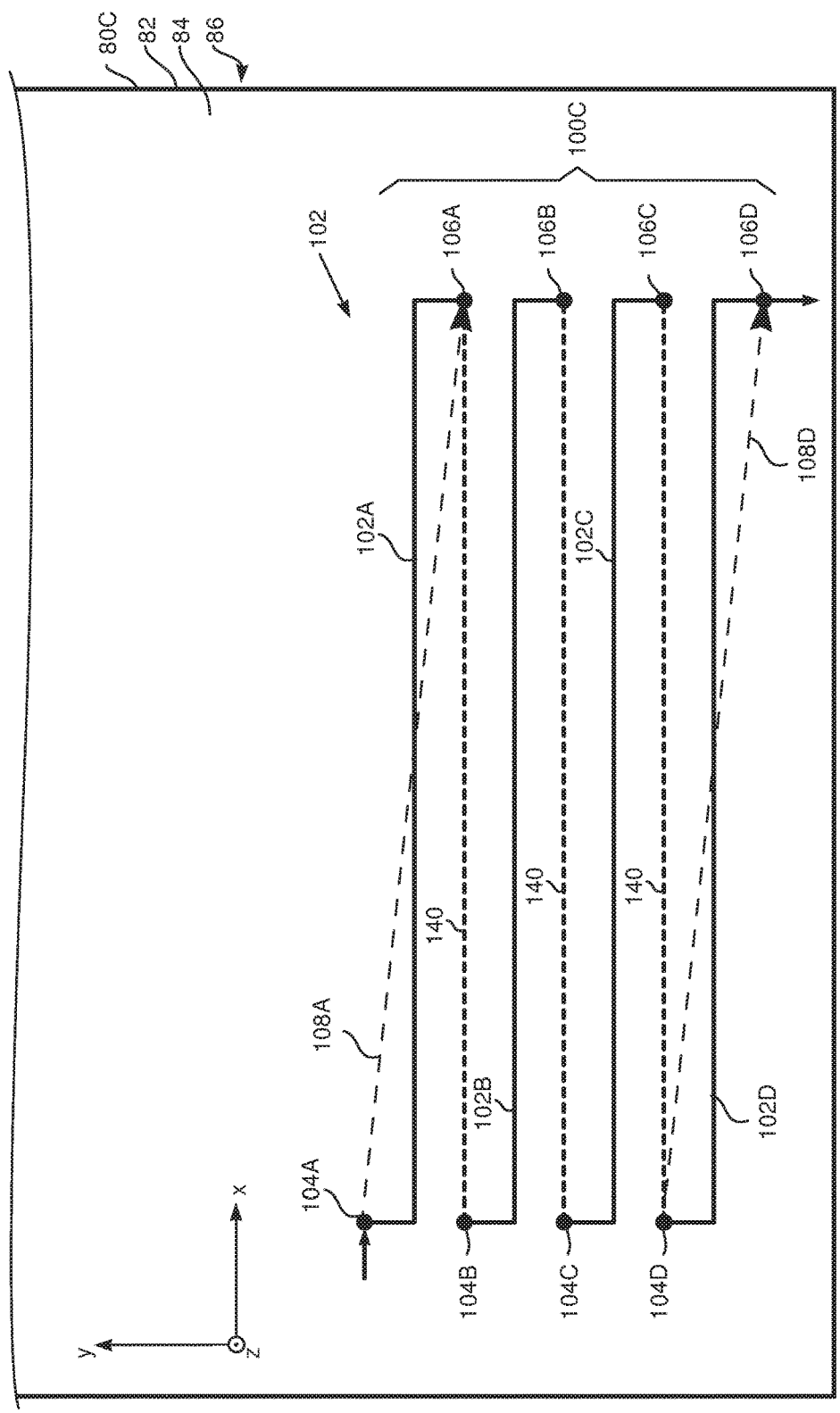
Figure 6C:
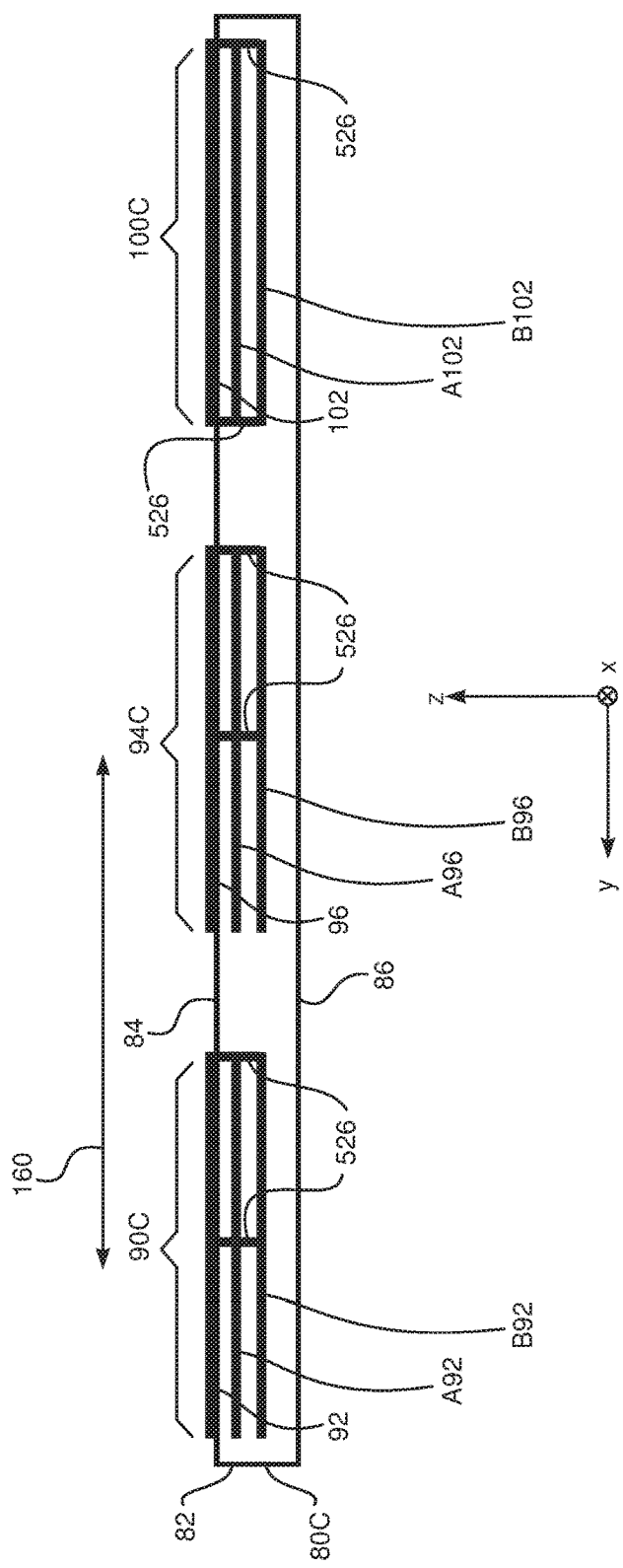

FIGS. 6A, 6B, and 6C are schematic diagrams illustrating a flexible sheet 80C used to produce a sensor 524, and FIG. 7 is a schematic diagram illustrating how the sheet is rolled up to form the sensor, according to an embodiment of the present invention. FIG. 6A illustrates a top portion of sheet 80C, and FIG. 6B illustrates a bottom portion of the sheet, both figures being viewed from above the sheet. FIG. 6C is a side view of sheet 80C. FIG. 7 is a schematic perspective view of the formed sensor.

Apart from the differences described below, the operation of sensor 524 is generally similar to that of sensor 24 (FIGS. 1-5A), and elements indicated by the same reference numerals in both sensors 24 and 524 are generally similar in construction and in operation. As for sensor 24, sensor 524 comprises three coils oriented orthogonally to each other.

Sensor 24 is formed from single sheet 80, which has single layers of conducting elements on conducting side 84 of the sheet for each of its coils, and there are no conducting elements within substrate 82 of the sheet. Sensor 524 is also formed from a single sheet 80C, which also has single layers of conducting elements on conducting side 84 of the sheet. However, in addition, in sheet 80C there are one or more conducting elements, similar to and aligned with those on the conducting side, embedded in respective layers within substrate 82 of the sheet. As is described below, the multiple sets of aligned conducting elements are connected in parallel by vias.

By way of example, in sheet 80C of sensor 524 there are two layers of conducting elements embedded in substrate 82, but embodiments of the present invention comprise any number of layers of conducting elements embedded in the substrate.

A set 90C of conducting elements comprises a plurality of spiral conductors 92, the same plurality of spiral conductors A92, and the same plurality of spiral conductors B92 (FIG. 6C). Spiral conductors 92 have been described above with reference to FIG. 2A. Spiral conductors A92 and B92 are congruent to spiral conductors 92, but are displaced from conductors 92 in the z direction. The initial terminations of the three sets of spiral conductors are connected by conducting vias 526, and the final terminations of the three sets are also connected by conducting vias 526. It will be understood that in set 90C there are four groups of spirals, each group comprising three spirals connected, by vias 526, in parallel.

A set 94C of conducting elements comprises a plurality of spiral conductors 96, the same plurality of spiral conductors A96, and the same plurality of spiral conductors B96. Spiral conductors 96 have been described above with reference to FIG. 2A. Spiral conductors A96 and B96 are congruent to spiral conductors 96, but are displaced from conductors 96 in the z direction. The initial terminations of the three sets of spiral conductors are connected by conducting vias 526, and the final terminations of the three sets are also connected by conducting vias 526. As for set 90C, in set 94C there are four groups of spirals, each group comprising three spirals connected, by vias 526, in parallel.

A set 100C of conducting elements comprises a plurality of conductive lines 102, the same plurality of lines A102, and the same plurality of lines B102. Lines 102 have been described above with reference to FIG. 2B. Lines A102 and B102 are congruent to lines 102, but are displaced from lines 102 in the z direction. The initial terminations of the three sets of conductive lines are connected by conducting vias 526, and the final terminations of the three sets are also connected by conducting vias 526. In set 100C there are four groups of lines, each group comprising three lines connected, by vias 526, in parallel.

When sheet 80C is rolled up to form sensor 524, the different groups of spirals and lines are connected by vias 132, 130, and 140, as illustrated in FIGS. 6A and 6B. The connections are as described above with reference to sensor 24, with the difference being that in sensor 24 vias 132 and 130 connect single spirals, whereas in sensor 524 vias 132 and 130 connect sets of spirals, each set comprising three spirals already connected in parallel. Similarly, in sensor 524 vias 140 connect sets of conductive lines, each set comprising three lines already connected in parallel.

Figure 8B:
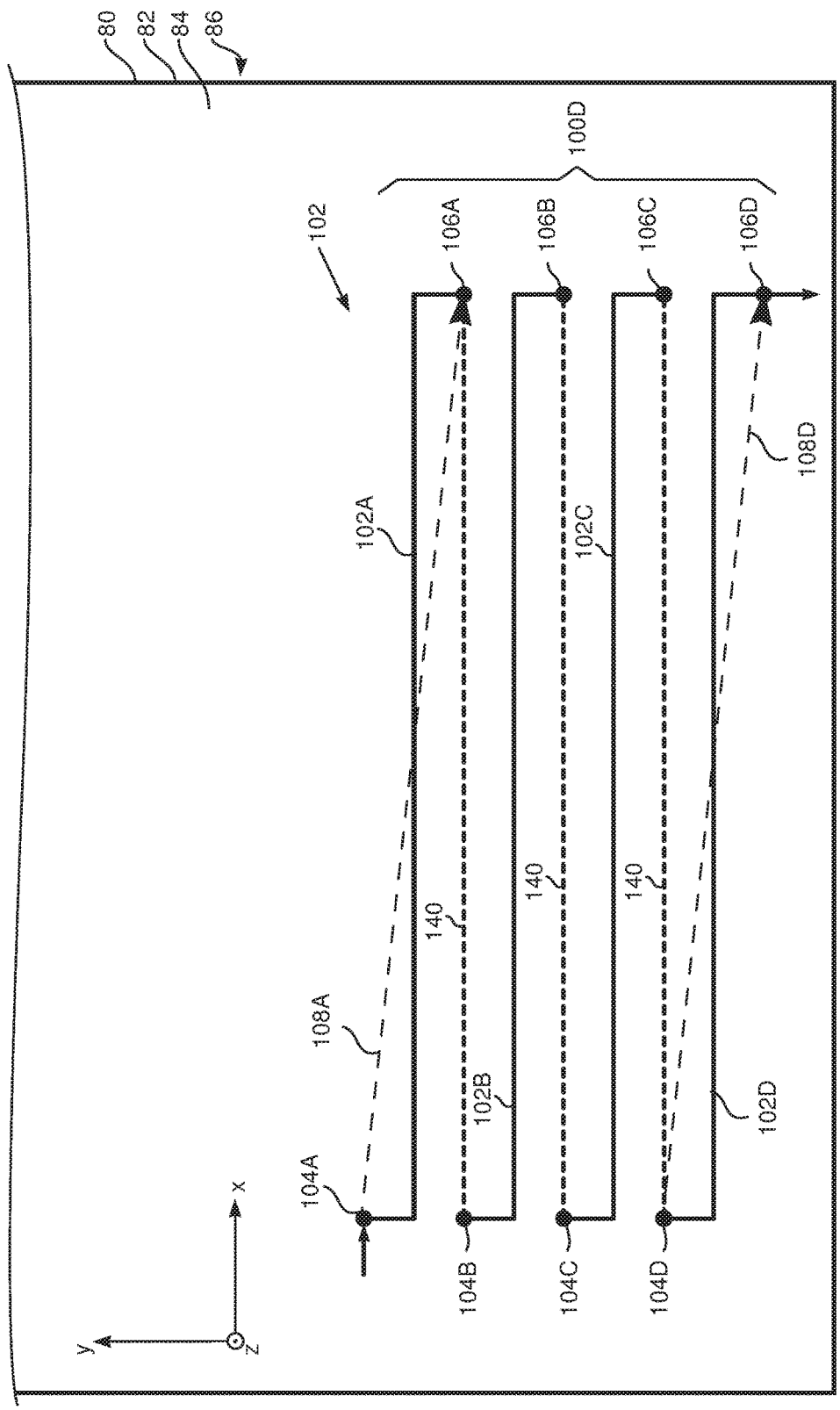
Figure 9:
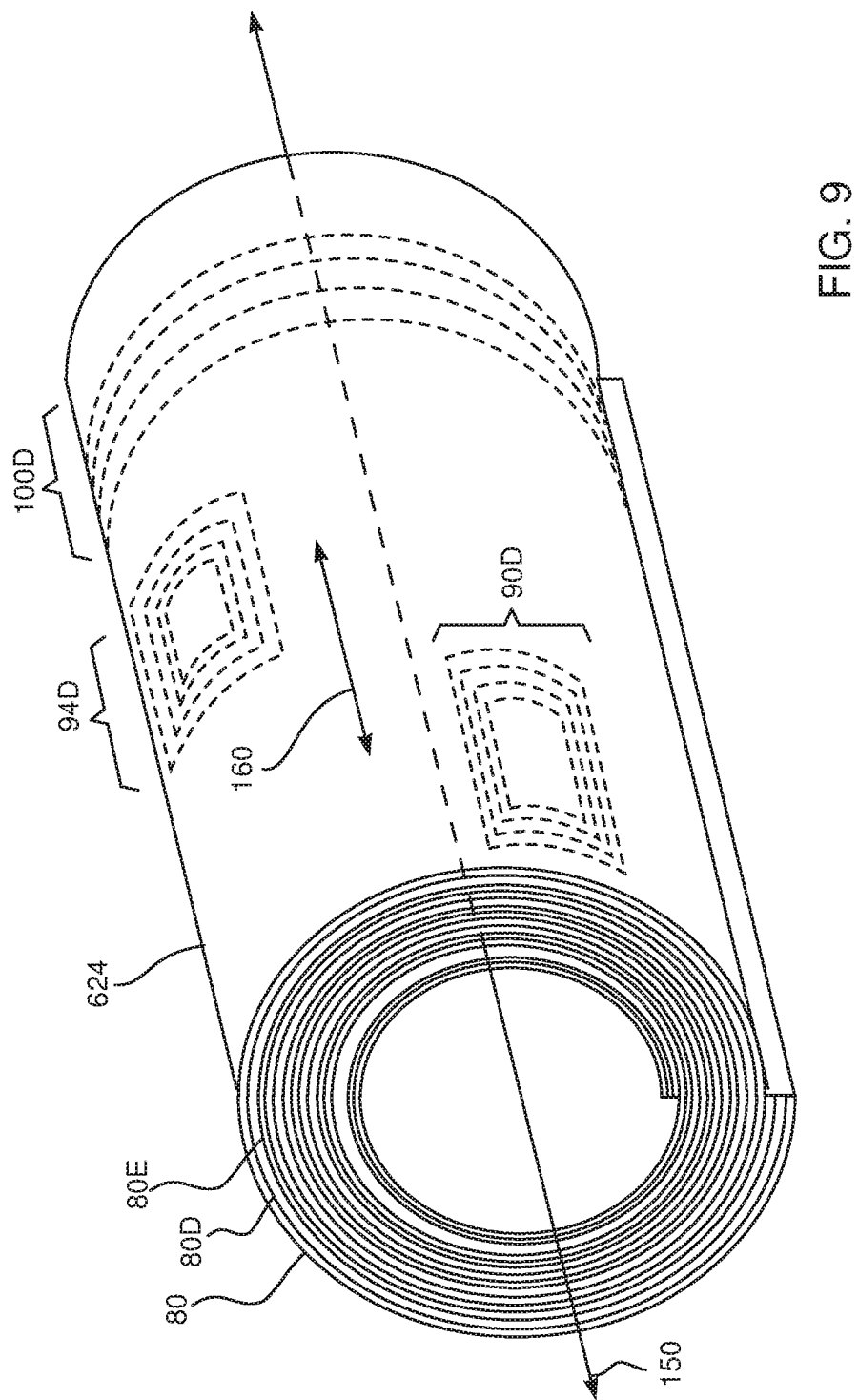
FIG. 9 is a schematic diagram illustrating how the sheets are rolled up to form the sensor, according to an embodiment of the present invention.

FIGS. 8A, 8B, and 8C are schematic diagrams illustrating flexible sheets 80, 80D, and 80E used to produce a sensor 624, and FIG. 9 is a schematic diagram illustrating how the sheets are rolled up to form the sensor, according to an embodiment of the present invention. FIG. 8A illustrates a top portion of upper sheet 80, and FIG. 8B illustrates a bottom portion of the upper sheet, both figures being viewed from above the sheet. FIG. 8C is a side view of the three sheets 80, 80D, and 80E. FIG. 9 is a schematic perspective view of the formed sensor.

Apart from the differences described below, the operation of sensor 624 is generally similar to that of sensor 24 (FIGS. 1-5A), and elements indicated by the same reference numerals in both sensors 24 and 624 are generally similar in construction and in operation. As for sensor 24, sensor 624 comprises three coils oriented orthogonally to each other.

In contrast to sensor 24, sensor 624 is formed from a plurality of substantially similar single sheets. By way of example, sensor 624 is assumed to be formed from three sheets 80, 80D, and 80E. However, embodiments of the present invention may form sensors from any number of substantially identical sheets. Sheets 80D and 80E are substantially identical to each other and to sheet 80, described above with reference to sensor 24.

Thus, sheets 80D and 80E have respective conducting sides 84D, 84E and non-conducting sides 86D, 86E (FIG. 8C). On conducting side 84D there are a plurality of spiral conductors D92 and D96, and a set of conductive lines D102, which are respectively congruent to spiral conductors 92, 96 and lines 102. Also, on conducting side 84E there are a plurality of spiral conductors E92 and E96, and a set of conductive lines E102, which are respectively congruent to spiral conductors 92, 96 and lines 102.

Prior to rolling up, sheets 80, 80D, and 80E are stacked on each other so that the conducting side of one sheet contacts the non-conducting side of an abutting sheet, and so that congruent elements in each sheet align. Thus, as shown in FIG. 8C, sheet 80 overlays sheet 80D, which in turn overlays sheet 80E.

Once aligned, initial and final terminations of congruent conducting elements in each of the sheets are connected together, by vias, to form parallel configurations. Thus, the initial and final terminations of spiral conductors 92, D92, and E92 are connected together by vias 526, as is illustrated in FIG. 8C, to form a set 90D of spiral conducting elements. It will be understood that set 90D comprises four groups of spirals, each group comprising three spirals connected in parallel by vias 526.

Similarly, the initial and final terminations of spiral conductors 96, D96, and E96 are connected together by vias 526 to form a set 94D of spiral conducting elements. Set 94D comprises four groups of spirals, each group comprising three spirals connected in parallel by vias 526.

In addition, the initial and final terminations of conductive lines 102, D102, and E102 are connected together by vias 526 to form a set 102D of conducting line elements. Set 102D comprises four groups of conductive line elements, each group comprising three conductive line elements connected in parallel by vias 526.

Sensor 24 is formed on single sheet 80, which has single layers of conducting elements on conducting side 84 of the sheet for each of its coils, and there are no conducting elements within substrate 82 of the sheet. Sensor 524 is formed on a single sheet 80C, which also has single layers of conducting elements on conducting side 84 of the sheet. However, in addition, in sheet 80C there are one or more conducting elements, similar to and aligned with those on the conducting side, embedded in respective layers within substrate 82 of the sheet. As is described below, the multiple sets of aligned conducting elements are connected in parallel by vias.

When sheets 80, 80D, and 80E are rolled up to form sensor 624, the different groups of spirals and lines are connected by vias 132, 130, and 140, as illustrated in FIGS. 8A and 8B. The connections are as described above with reference to sensor 24, with the difference being that in sensor 24 vias 132 and 130 connect single spirals, whereas in sensor 624 vias 132 and 130 connect sets of spirals, each set comprising three spirals already connected in parallel. Similarly, in sensor 624 vias 140 connect sets of conductive lines, each set comprising three lines already connected in parallel.

Figure 10:
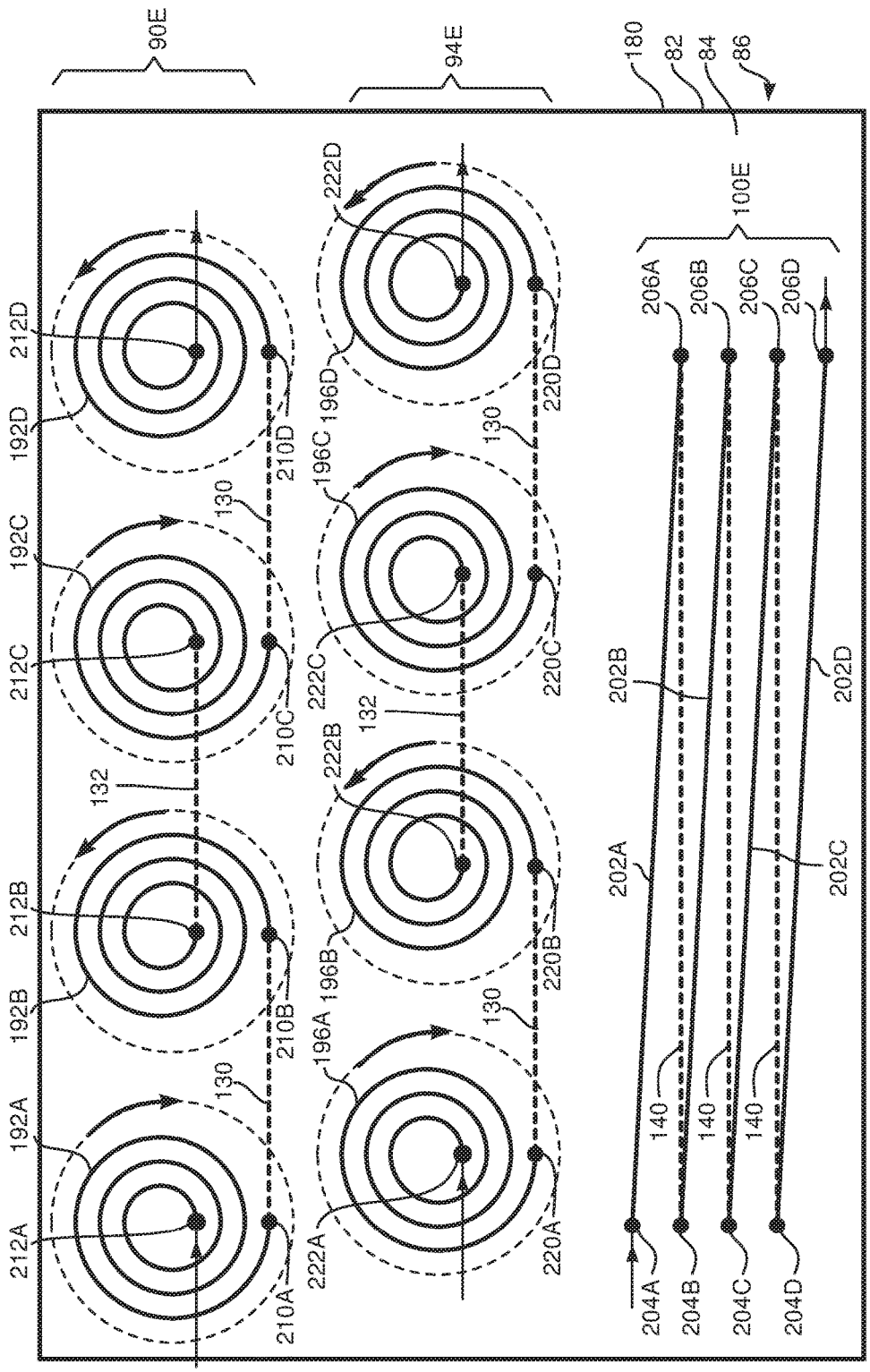
FIG. 10 is a schematic diagram illustrating a flexible sheet used to produce a sensor.
Figure 11:
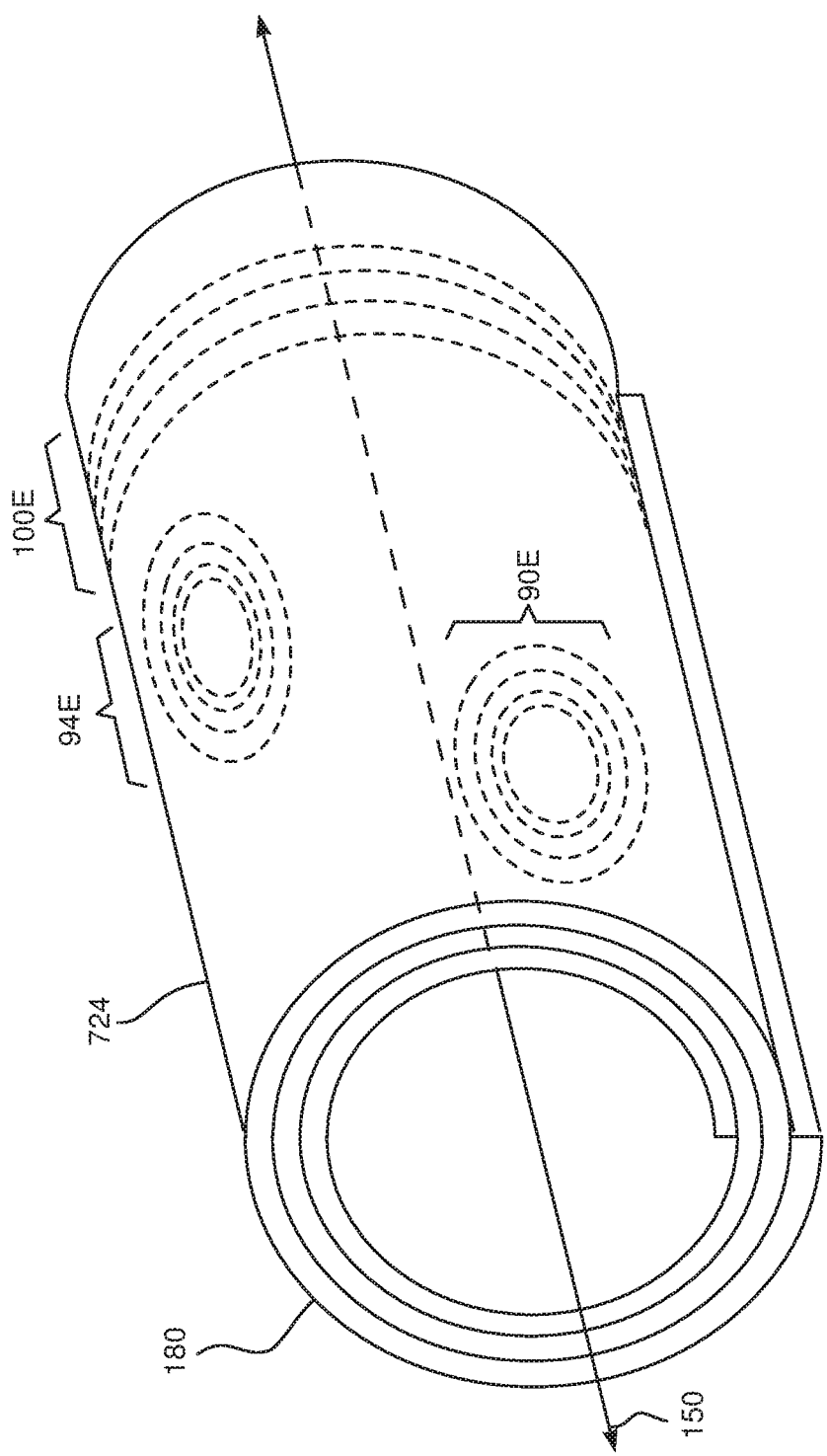
FIG. 11 is a schematic diagram illustrating how the sheet is rolled up to form the sensor, according to an embodiment of the present invention.

FIG. 10 is a schematic diagram illustrating a flexible sheet 180 used to produce a sensor 724, and FIG. 11 is a schematic diagram illustrating how the sheet is rolled up to form the sensor, according to an embodiment of the present invention. Apart from the differences described below, the operation of sensor 724 is generally similar to that of sensor 24 (FIGS. 1-5A), and elements indicated by the same reference numerals in both sensors 24 and 724 are generally similar in construction and in operation.

In contrast to sensor 24, wherein the elements of the sensor are formed from rectilinear conducting elements having sections which are orthogonal to each other, the elements of two sets 90E, 94E of spiral conducting elements of sensor 724 are formed from curvilinear elements. Also in contrast to sensor 24, the conducting lines of a third set 100E of conducting lines of the sensor do not have initial terminations and final terminations which are offset from the lines; rather each conducting line of the third coil of sensor 724 is a line, typically a straight line, from its initial to its final termination.

Set 90E comprises four curvilinear spirals 192A, 192B, 192C, and 192D which have respective initial terminations 210A, 210B, 210C, 210D and final terminations 212A, 212B, 212C, 212D, and as for set 90 of sensor 24, the spirals of set 90E are positioned on a straight line segment and adjacent spirals are mirror images of each other. Thus, as illustrated by the arrows around the spirals in FIG. 10, spiral conductors 192A, 192C rotate in a right handed direction, and spiral conductors 192B, 192D rotate in a left handed direction.

As for sensor 24, in the rolled up configuration of sensor 724, the spirals of set 90E align with themselves, so that initial terminations 210A, 210B, 210C, 210D align with themselves, and final terminations 212A, 212B, 212C, 212D also align with themselves.

As for the rolled up configuration of sensor 24, in the rolled up configuration of sensor 724, except for end spirals, an initial termination is connected by a via to an initial termination of an adjacent spiral, and a final termination is connected by a via to a final termination. In the example illustrated, vias 130 connect initial terminations 210A and 210B, 210C and 210D, and a via 132 connects final terminations 212B and 212C. End spirals 192A, 192D each have a respective final termination not connected to another spiral.

Except for the following differences, the spirals of set 94E are generally similar in layout and configuration to the spirals of set 90E. Thus, the four example spirals in the figure have initial terminations 220A, 220B, 220C, 220D and final terminations 222A, 222B, 222C, 222D. As for set 90E, in set 94E adjacent spirals are typically mirror images, in a mirror plane centered between the spirals, so that the spirals alternate between rotating in a right handed direction around a normal to sheet 180 and in a left handed direction about the normal.

The spirals of set 94E are also positioned along a straight line segment parallel to the 90E line segment, and the spirals have substantially the same separations on their line segment as the spirals of set 90E. In the rolled up configuration of sensor 724 the spirals of set 94E align with themselves, as do the initial and final terminations of the set. The terminations are also connected, by vias 130 and 132, as is illustrated in FIG. 10.

As for sensor 24, the line segment for set 94E is displaced relative to the line segment of set 90E. The displacement is substantially as described above for sensor 24 and is such that in the rolled up configuration of sensor 724 an angle subtended by sets 90E and 94E to sensor axis 150 is 90°.

As stated above, third set 100E of conducting lines of sensor 724 do not have initial terminations and final terminations which are offset from the lines; rather each conducting line of the third set, that forms a third coil of sensor 724, is a line, herein assumed to be a straight line, from its initial to its final termination. Thus conducting lines 202A, 202B, 202C, and 202D are lines between respective initial terminations 204A, 204B, 204C, and 204D and respective final terminations 206A, 206B, 206C, and 206D.

In sensor 724 rays from the initial termination to the final termination of a given conducting line of set 100E have a common direction.

As for sensor 24, in sensor 724 the conducting lines of set 100E are displaced relative to each other, parallel to sensor axis 150, so that in the rolled up configuration of the sensor the initial termination of a given line in set 100E aligns with the final termination of a neighboring line on the set. This alignment applies except for the initial termination of a "first" line of set 100E and for the final termination of a "last" line of the set, which are not aligned with any terminations. In addition, the aligned terminations are connected by vias.

Thus, as illustrated in FIG. 10, in the rolled up configuration of sensor 724, initial termination 204B aligns with, and is connected by a via 140 to, final termination 206A; initial termination 204C aligns with, and is connected by a via 140 to, final termination 206B; and initial termination 204D aligns with, and is connected by a via 140 to, final termination 206C. As for sensor 24, in sensor 724 vias 140 penetrate through the first side of sheet 180 to the second side of the sheet to interconnect the initial termination of a given line with the final termination of a neighboring line.

As is apparent from the description above and from FIG. 10, each of sets 90E, 94E, and 100E have two "free" terminations. If current is input to one of the free terminations of a coil it exits from the other free termination, as is illustrated by the arrows at terminations 212A and 212D, 222A and 222D, and 204A and 206D, and the current traverses all the elements of a given set in a common direction. Thus, as for sensor 24, the via connected sets of sensor 724 behave as respective coils of wire.

The embodiments described above comprise rectilinear and curvilinear conducting lines, which are connected by vias to form coils. However, it will be understood that embodiments of the present invention are not limited to one type of conducting line, but may comprise mixtures of such lines. Furthermore, rectilinear conducting lines do not necessarily comprise sections which are orthogonal to each other, but rather may comprise sections making any convenient angles with each other, such as being sections of a hexagon or an octagon. In addition, in the case of the conducting lines comprising sets such as set 100, it will be understood that at least a part of such lines may be curvilinear.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. Apparatus, comprising:
   a flexible insulating substrate, having a first side and a second side, rolled about an axis parallel to the substrate;
   a first planar conducting spiral that is right-handed relative to a normal to the substrate, and a second planar conducting spiral that is left-handed relative to the normal, formed on the first side of the substrate,
   the first conducting spiral having a first initial termination and a first final termination,
   the second conducting spiral having a second initial termination and a second final termination,
   the spirals having a displacement therebetween, with a preset magnitude so that when the substrate is rolled about the axis the first initial termination aligns with the second initial termination;
   and a via penetrating the substrate from the first side to the second side so as to interconnect the first initial termination and the second initial termination;
   a third planar conducting spiral that is right-handed relative to the normal to the substrate, and a fourth planar conducting spiral that is left-handed relative to the normal, formed on the first side of the substrate,
   the third conducting spiral having a third initial termination and a third final termination, the fourth conducting spiral having a fourth initial termination and a fourth final termination,
   the third and the fourth spirals having the displacement with the preset magnitude therebetween,
   and wherein a first line segment joining the third and the fourth spirals has a second displacement from a second line segment joining the first and the second spirals, and so that when the substrate is rolled about the axis the third initial termination aligns with the fourth initial termination;
   and a second via penetrating the substrate from the first side to the second side so as to interconnect the third initial termination and the fourth initial termination.

2. The apparatus according to claim 1, wherein at least one of the first and the second conducting spirals comprises a rectilinear element.

3. The apparatus according to claim 1, wherein at least one of the first and the second conducting spirals comprises a curvilinear element.

4. The apparatus according to claim 1, wherein when the substrate is rolled about the axis the first final termination aligns with the second final termination.

5. The apparatus according to claim 1, wherein the first conducting spiral is a mirror image of the second conducting spiral.

6. The apparatus according to claim 1, and comprising:
   a third planar conducting spiral that is right-handed relative to the normal to the substrate, formed on the first side of the substrate, and that comprises a third initial termination and a third final termination, the third spiral having a further displacement from the second spiral so that when the substrate is rolled about the axis the second final termination aligns with the third final termination; and a second via penetrating the substrate from the first side to the second side so as to interconnect the second final termination and the third final termination.

7. The apparatus according to claim 1, wherein when the substrate is rolled about the axis an angle between a first line, from the first spiral to the axis, and a second line, from the third spiral to the axis, is 90°.

8. The apparatus according to claim 1, wherein when the substrate is rolled about the axis a first plane, containing a first line from the first spiral to the axis and orthogonal to the axis, is disjoint from a second plane, containing a second line from the third spiral to the axis and orthogonal to the axis.

9. The apparatus according to claim 1, wherein the second displacement is parallel to the axis.

10. The apparatus according to claim 1, and comprising a magnetic tracking system, and wherein, when the substrate is rolled about the axis and the via interconnects the first and second initial terminations the first and second conducting spirals operate as a sensing coil in the magnetic tracking system.

\* \* \* \* \*